US009528161B2

(12) United States Patent
Willey et al.

(10) Patent No.: US 9,528,161 B2
(45) Date of Patent: Dec. 27, 2016

(54) MATERIALS AND METHODS FOR QUALITY-CONTROLLED TWO-COLOR RT-QPCR DIAGNOSTIC TESTING OF FORMALIN FIXED EMBEDDED AND/OR FRESH-FROZEN SAMPLES

(71) Applicant: The University of Toledo, Toledo, OH (US)

(72) Inventors: James C. Willey, Toledo, OH (US); Jiyoun Yeo, Maumee, OH (US); Erin Crawford, Rossford, OH (US)

(73) Assignee: The University of Toledo, Toledo, OH (US)

( * ) Notice: Subject to any disclaimer, the term of this patent is extended or adjusted under 35 U.S.C. 154(b) by 99 days.

(21) Appl. No.: 14/619,285

(22) Filed: Feb. 11, 2015

(65) Prior Publication Data

US 2015/0225798 A1 Aug. 13, 2015

Related U.S. Application Data

(60) Provisional application No. 61/939,060, filed on Feb. 12, 2014.

(51) Int. Cl.
*C12Q 1/68* (2006.01)
*G06F 19/24* (2011.01)

(52) U.S. Cl.
CPC .......... *C12Q 1/6886* (2013.01); *C12Q 1/6851* (2013.01); *C12Q 2600/158* (2013.01); *C12Q 2600/166* (2013.01); *G06F 19/24* (2013.01)

(58) Field of Classification Search
None
See application file for complete search history.

(56) References Cited

PUBLICATIONS

Crawford et al. (Multiplex standardized RT-PCR for expression analysis of many genes in small samples. Biochem Biophys Res Commun 293: 509-516.).*

Yeo (A multiplex two-color real-time PCR method for quality-controlled molecular diagnostic testing of FFPE samples, (May 2014).Theses and Dissertations. Paper 1595).*

* cited by examiner

*Primary Examiner* — Aaron Priest

(74) *Attorney, Agent, or Firm* — MacMillan, Sobanski & Todd, LLC

(57) ABSTRACT

Described herein are materials, methods, and kits enabling accurate and reproducible two-color reverse-transcription real-time quantitative PCR (RT-qPCR) for quality-controlled molecular diagnostic testing of samples that may contain degraded RNA. In certain aspects described herein are materials, methods, and kits for use in the molecular diagnostic testing of lung cancer in FFPE samples and/or fresh-frozen samples. Also described herein are materials and methods to control for inter-experimental variation occurring during two-color RT-qPCR amplification arising from variation in fluorescence specific activity, use of different thermocyclers, and inter-laboratory differences.

31 Claims, 28 Drawing Sheets
(9 of 28 Drawing Sheet(s) Filed in Color)

Experiment Setup in 96 Well Plate

- 1st round PCR
  - 20 Samples: Each sample cDNA was mixed with aliquot of ISM and pre-amplified.

- 2nd round PCR
  - Measure each gene relative to known number of IS molecules within ISM
  - Measure four genes/Sample
  - Measure each gene in ESM at $10^{-13}$ M and $10^{-14}$M
  - No template control (control for false positives)

- Two External Standards Plot
  - 10-13M, 10-14M
  - e.g.) ACTB

| | MYC | E2F1 | CDKN1A | LCDT |
|---|---|---|---|---|
| ■ 2V, 1Pm, 1Pb | 6.6E+03 | 1.9E+03 | 2.4E+04 | 5.9E+02 |
| ▩ 2V, 2Pm, 1Pb | 6.8E+03 | 2.3E+03 | 2.2E+04 | 7.3E+02 |
| □ 2V, 1Pm, 2Pb | 6.7E+03 | 2.0E+03 | 2.0E+04 | 7.0E+02 |
| ▩ 1V, 1Pm, 1Pb | 7.0E+03 | 1.9E+03 | 2.2E+04 | 6.2E+02 |
| ▩ 1V, 2Pm, 1Pb | 5.0E+03 | 1.6E+03 | 1.7E+04 | 4.8E+02 |
| ▩ 1V, 1Pm, 2Pb | 6.6E+03 | 1.8E+03 | 1.9E+04 | 6.5E+02 |

| | MYC | E2F1 | CDKN1A | LCDT |
|---|---|---|---|---|
| ■ 2V, 1Pm, 1Pb | 7.2E+03 | 2.5E+03 | 2.0E+04 | 8.9E+02 |
| ▩ 2V, 2Pm, 1Pb | 8.6E+03 | 2.8E+03 | 2.1E+04 | 1.2E+03 |
| □ 2V, 1Pm, 2Pb | 8.9E+03 | 2.7E+03 | 1.7E+04 | 1.2E+03 |
| ■ 1V, 1Pm, 1Pb | 7.8E+03 | 2.2E+03 | 1.9E+04 | 8.6E+02 |
| ▩ 1V, 2Pm, 1Pb | 7.6E+03 | 2.5E+03 | 1.9E+04 | 8.4E+02 |
| □ 1V, 1Pm, 2Pb | 9.5E+03 | 3.7E+03 | 1.7E+04 | 1.5E+03 |

Inter-experimental variation in Cq threshold

| Day | ACTB-NT | ACTB-IS | MYC-NT | MYC-IS |
|---|---|---|---|---|
| #1 | 0.18 | 0.04 | 0.03 | 0.10 |
| #2 | 0.24 | 0.02 | 0.36 | 0.03 |
| #3 | 0.24 | 0.03 | 0.31 | 0.04 |
| #4 | 0.21 | 0.02 | 0.28 | 0.07 |
| #5 | 0.02 | 0.02 | 0.07 | 0.04 |

FIG. 11E

| Sample | Day | ISM | NT Cq | IS Cq | Raw ΔCq | | ESM ΔCq | | Corrected ΔCq | ACTB molec. With ESM | ACTB molec. Without ESM |
|---|---|---|---|---|---|---|---|---|---|---|---|
| SM8 | #1 | D(-12/-14) | 11.7 | 13.0 | -1.3 | | -2.0 | | 0.7 | 3.8E+05 | 1.5E+06 |
| | #2 | D(-12/-14) | 11.8 | 11.3 | 0.5 | | 0.0 | | 0.4 | 4.5E+05 | 4.3E+05 |
| | | E(-12/-15) | 11.7 | 11.0 | 0.7 | - | 0.0 | = | 0.6 | 3.8E+05 | 3.7E+05 |
| | #3 | D(-12/-14) | 11.6 | 10.8 | 0.8 | | -0.6 | | 1.4 | 2.3E+05 | 3.4E+05 |
| | | E(-12/-15) | 12.2 | 11.2 | 1.0 | | -0.6 | | 1.6 | 2.0E+05 | 3.0E+05 |
| | #4 | D(-12/-14) | 18.0 | 16.6 | 1.4 | | 0.5 | | 0.9 | 3.3E+05 | 2.3E+05 |
| | #5 | D(-12/-14) | 12.1 | 13.6 | -1.5 | | -2.1 | | 0.6 | 3.9E+05 | 1.7E+06 |
| **CV** | | | | | | | | | | **0.27** | **0.90** |

FIG. 11F 100
80
60
40
20
0
Sensitivity
0 20 40 60 80 100
100% - Specificity%

| Malignant | RNA (ng) | A260/280 | Benign | RNA (ng) | A260/280 |
|---|---|---|---|---|---|
| **SM1** | 16100 | 2.00 | **SB1** | 21200 | 2.02 |
| **SM2** | 18100 | 2.00 | **SB2** | 2900 | 1.92 |
| **SM3** | 45800 | 2.04 | **SB3** | 36100 | 2.15 |
| **SM4** | 8400 | 2.02 | **SB4** | 17900 | 2.02 |
| **SM5** | 55400 | 2.13 | **SB5** | 20300 | 2.16 |
| **SM6** | 79700 | 2.09 | **SB6** | 41800 | 2.13 |
| **SM7** | 80400 | 2.03 | **SB7** | 3400 | 1.79 |
| **SM8** | 36300 | 2.05 | **SB8** | 17700 | 2.02 |
| **SM9** | 103400 | 2.03 | **SB9** | 10400 | 1.90 |
| **SM10** | 24600 | 2.00 | **SB10** | 7300 | 2.04 |
| **Ave.** | **46800 ng** | | **Ave.** | **17900 ng** | |

FIG. 14A cont.

| Malignant | RNA (ng) | A260/280 | Benign | RNA (ng) | A260/280 |
|---|---|---|---|---|---|
| NM1 | 320 | 1.58 | NB1 | 590 | 1.53 |
| NM2 | 870 | 1.84 | NB2 | 240 | 1.89 |
| NM3 | 750 | 1.91 | NB3 | 12 | 2.48 |
| NM4 | 240 | 1.61 | NB4 | 100 | 1.78 |
| NM5 | 300 | 1.64 | NB5 | 1100 | 1.6 |
| NM6 | 500 | 1.95 | | | |
| NM7 | 200 | 2.17 | | | |
| NM8 | 130 | 1.7 | | | |
| NM9 | 220 | 2.09 | | | |
| NM10 | 12 | -5.61 | | | |
| NM11 | 1230 | 2.08 | | | |
| NM12 | 850 | 1.99 | | | |
| NM13 | 130 | 1.78 | | | |
| Ave. | 440 ng | | Ave. | 400 ng | |

FIG. 14B cont.

MATERIALS AND METHODS FOR QUALITY-CONTROLLED TWO-COLOR RT-QPCR DIAGNOSTIC TESTING OF FORMALIN FIXED EMBEDDED AND/OR FRESH-FROZEN SAMPLES

CROSS-REFERENCE TO RELATED APPLICATIONS

This application claims priority to U.S. Provisional Application No. 61/939,060, filed Feb. 12, 2014, the entire disclosure of which is expressly incorporated herein by reference for all purposes.

STATEMENT REGARDING FEDERALLY SPONSORED RESEARCH

This invention was made with government support under Grant No. CA138397 awarded by NCI/NIH and Grant No. CA132806 awarded by NCI/NIH. The government has certain rights in this invention.

SEQUENCE LISTING

The instant application contains a Sequence Listing which has been submitted via EFS-web and is hereby incorporated by reference in its entirety. The ASCII copy, created on Feb. 10, 2015, is named 1-55871-UT-D2013-65_SL.txt, and is 8,446 bytes in size.

| Gene | Description | Sequence | SEQ ID NO |
|---|---|---|---|
| ACTB (NM_001101.3) | Forward Primer | GCCCTGAGGCACTCTTCCAG | 1 |
| | Reverse Primer | TTTCGTGGATGCCACAGGAC | 2 |
| CDKN1A (NM_000389.4 | Forward Primer | CCTGGAGACTCTCAGGGTCG | 3 |
| | Reverse Primer | GCGTTTGGAGTGGTAGAAAT | 4 |
| MYC (NM_002467.4) | Forward Primer | AGCTGCTTAGACGCTGGATT | 5 |
| | Reverse Primer | CTAACGTTGAGGGGCATCGT | 6 |
| E2F1 (NM_005225.2) | Forward Primer | CTCCTCAGGGCACAGGAA | 7 |
| | Reverse Primer | CGTGGACTCTTCGGAGAACTTTC | 8 |
| ACTB (NM_001101.3) | NT Probe 5' FAM | CCTTCCTTCCTGGGCATG | 9 |
| | IS Probe 5' Quasar 670 | CC***AA***CCTTCC***A***GGGCAT***C*** | 10 |
| CDKN1A (NM_000389.4 | NT Probe 5' FAM | AAACGGCGGCAGACCAGC | 11 |
| | IS Probe 5' Quasar 670 | ***TT***ACGGCGG***GT***GACCA***C*** | 12 |
| MYC (NM_002467.4) | NT Probe 5' FAM | TAGTGGAAAACCAGCAGCCT | 13 |
| | IS Probe 5' Quasar 670 | ***AT***GTGGAAA***T***CC***T***GCAGC***GA*** | 14 |
| E2F1 (NM_005225.2) | NT Probe 5' FAM | CATCGATCGGGCCTTGTT | 15 |
| | IS Probe 5' Quasar 670 | ***TT***CCGATCG***T***GCCTTCTA | 16 |
| ACTB (NM_001101.3) | NT Sequence | GCCCTGAGGCACTCTTCCAGCCTTCCTTCCTGGGCATGG AGTCCTGTGGCATCCACGAAA | 17 |
| | IS Sequence | GCCCTGAGGCACTCTTCCAGCCAACCTTCCAGGGCATCG AGTCCTGTGGCATCCACGAAA | 18 |
| CDKN1A (NM_000389.4 | NT Sequence | CCTGGAGACTCTCAGGGTCGAAAACGGCGGCAGACCAG CATGACAGATTTCTACCACTCCAAACGC | 19 |
| | IS Sequence | CCTGGAGACTCTCAGGGTCGATTACGGCGGGTGACCAC CATGACAGATTTCTACCACTCCAAACGC | 20 |
| MYC (NM_002467.4) | NT Sequence | AGCTGCTTAGACGCTGGATTTTTTTCGGGTAGTGGAAA ACCAGCAGCCTCCCGCGACGATGCCCCTCAACGTTAG | 21 |
| | IS Sequence | AGCTGCTTAGACGCTGGATTTTTTTCGGGATGTGGAAAT CCTGCAGCGACCCGCGACGATGCCCCTCAACGTTAG | 22 |

-continued

| Gene | Description | Sequence | SEQ ID NO |
|---|---|---|---|
| E2F1 (NM_005225.2) | NT Sequence | CTCCTCAGGGCACAGGAAAACATCGATCGGGCCTTGTT TGCTCTTAAGGGAGATCTGAAAGTTCTCCGAAGAGTCC ACG | 23 |
| | IS Sequence | CTCCTCAGGGCACAGGAAAA***TTC***CGATCG***T***GCCTT***C***T***A***T GCTCTTAAGGGAGATCTGAAAGTTCTCCGAAGAGTCCA CG | 24 |

BACKGROUND OF THE INVENTION

Reverse transcription quantitative real-time polymerase chain reaction (RT-qPCR) tests that measure transcript abundance of selected genes in clinical specimens have been demonstrated to increase cancer diagnostic accuracy and enable "personalized medicine" through selection of the most effective treatment for each cancer.

There are challenges to using such methods, however, and these methods do not work well when the amount of sample is small or when the sample contains degraded RNA.

A particular challenge is that current clinical pathology sample collection and processing procedures focus on formalin fixation and paraffin embedding (FFPE) and fresh/fresh-frozen tissues rarely are available for molecular analysis. FFPE samples are difficult to work with because they yield RNA that 1) often contains PCR-interfering substances, and 2) is uniformly highly fragmented and often in low abundance. Economic factors prevent changing this workflow to ensure collection of samples in a form more conducive to molecular genetic analysis, such as fresh-frozen, therefore, there is a need to develop methods that are sufficiently robust to reliably conduct molecular genetic analysis in FFPE samples. These RT-qPCR tests must be able to assess FFPE samples with quality control and inter-laboratory reproducibility.

SUMMARY OF THE INVENTION

Described herein are materials, methods, and kits enabling accurate and reproducible two-color reverse-transcription real-time quantitative PCR (RT-qPCR) for quality-controlled molecular diagnostic testing of samples that may contain degraded RNA.

In a particular embodiment described herein is a kit for use in molecular diagnostic testing of a sample, comprising a) synthetic competitive internal standards (IS), wherein known quantities of each IS are formulated into an internal standards mixture (ISM); b) an external standards mixture (ESM) comprising 1) purified synthetic native template (NT), and 2) synthetic competitive internal standards (IS), wherein known quantities of each purified synthetic NT and IS are formulated into the ESM; c) pairs of gene-specific primers (GSP) specific to specific genes and primers; and d) sequence-specific fluorometric hydrolysis probes, wherein all fluorometric hydrolysis probes are labeled with a fluorescent reporter.

Another particular embodiment provided herein provides a method for using a kit described herein, comprising the steps of: a) extracting RNA from a sample; b) reverse-transcribing (RT) the RNA extracted from the sample; c) pre-amplifying cDNA generated by the RT of the RNA extracted from the sample along with the ISM, wherein the pre-amplification of the cDNA and ISM is done by polymerase chain reaction (PCR) using the pairs of GSP specific to the genes; d) performing a second round of PCR amplification for the genes, wherein a reaction mixture for a single gene comprises: 1) a dilution of the pre-amplified cDNA and ISM; 2) a primer mixture comprising the pairs of GSP corresponding to the genes; and 3) fluorometric hydrolysis probes specific for the single gene NT and corresponding IS; e) along with the second round of PCR amplification, for each gene, simultaneously performing PCR amplification on two distinct concentrations of the ESM, wherein each distinct concentration of ESM further comprises the same fluorometric hydrolysis probes specific for the single gene NT and corresponding IS of step d) 3); and f) quantifying the copy number for loading the genes (e.g., a control gene and one or more target genes).

In another particular embodiment provided herein is a method for using a kit described herein, wherein the step of quantifying the copy number for each target gene comprises the steps of: a) calculating the difference in quantification cycle (Cq) between the NT and IS for a target gene using the formula $[\text{NT Cq}-\text{IS Cq}]_{Target\ Gene}$; b) calculating an average difference in Cq between the NT and IS of two concentrations of ESM using the formula $([\text{NT Cq}-\text{IS Cq}]_{ESM\ Concentration\ 1}+[\text{NT Cq}-\text{IS Cq}]_{ESM\ Concentration\ 2})/2=[\text{NT Cq}-\text{IS Cq}]_{ESM}$; c) calculating a corrected delta Cq using the formula $[\text{NT Cq}-\text{IS Cq}]_{Target\ Gene}-[\text{NT Cq}-\text{IS Cq}]_{ESM}$; d) obtaining a target gene NT copy number by multiplying $2^{(-corrected\ delta\ Cq)}$ by a known number of input IS copies corresponding to the target gene in the reaction; and e) normalizing the target gene NT copy number to a gene loading control NT value.

In another particular embodiment provided herein is a method described herein, wherein the samples comprise material having degraded RNA therein.

In another particular embodiment provided herein is a method described herein, wherein the samples comprise formalin fixed paraffin embedded (FFPE) samples.

In another particular embodiment provided herein is a method described herein, wherein the samples comprise fresh-frozen samples.

In a particular embodiment described herein is a kit for use in molecular diagnostic testing of a sample comprising: a) one or more synthetic competitive internal standards (IS), wherein each IS is synthesized to correspond with a unique target gene or reference gene, wherein an IS probe binding site has a 4-6 bp difference than that of a native template (NT), and wherein known quantities of the one or more IS are formulated into an internal standards mixture (ISM); b) an external standards mixture (ESM) comprising: 1) one or more purified synthetic NT, wherein each NT is synthesized to correspond with a unique target gene or reference gene; and 2) one or more synthetic competitive internal standards (IS), wherein each IS is synthesized to correspond with a unique target gene or reference gene, wherein known quantities of each purified synthetic NT and IS are formulated into the ESM; c) one or more pairs of gene-specific primers (GSP), wherein each pair of GSP is specific for a unique target gene or reference gene, and is designed to amplify a PCR product having a product size of approximately 60-80 base pairs and span introns/exon splice junctions of the unique target gene or reference gene; and d) at least one pair of fluorometric hydrolysis probes, wherein each pair of fluorometric probes is specific for a particular target gene or reference gene, and comprises a first fluorometric hydrolysis probe that is sequence-specific for an NT probe binding site and is labeled with a first fluorescent reporter, and a second fluorometric hydrolysis probe that is sequence specific for an IS probe binding site of an IS corresponding to the NT against which the first fluorometric hydrolysis probe is sequence-specific for, and is labeled with a second fluorescent reporter.

Another particular embodiment provided herein provides a method for using a kit described herein, comprising the steps of: a) extracting RNA from the sample; b) reverse-transcribing (RT) the RNA extracted from the sample; c) pre-amplifying cDNA generated by the RT of the RNA extracted from the sample along with ISM including IS for each target gene or reference gene, wherein the pre-amplification of the cDNA and ISM is done by polymerase chain reaction (PCR) using the pairs of GSP specific to each target gene or reference gene; d) performing a second round of PCR amplification for each target gene and at least one reference gene, wherein a reaction mixture for a single target gene or reference gene comprises: 1) a dilution of the pre-amplified cDNA and ISM; 2) a primer mixture comprising the one or more pairs of GSP; and 3) one pair of fluorometric hydrolysis probes, specific for a single target gene or reference gene and its corresponding IS; e) along with the second round of PCR amplification, for each target gene or reference gene, simultaneously performing a PCR amplification on two distinct concentrations of the ESM containing the same pair of fluorometric hydrolysis probes used in step d) 3); and f) quantifying the copy number for each target gene.

In another particular embodiment provided herein is a method for using a kit described herein, wherein the step of quantifying the copy number for each target gene comprises the steps of: a) calculating the difference in quantification cycle (Cq) between the NT and IS for a target gene using the formula$[\text{NT Cq}-\text{IS Cq}]_{Target\ Gene}$; b) calculating an average difference in Cq between the NT and IS of two concentrations of ESM using the formula $([\text{NT Cq}-\text{IS Cq}]_{ESM\ Concentration\ 1}+[\text{NT Cq}-\text{IS Cq}]_{ESM\ Concentration\ 2})/2=[\text{NT Cq}-\text{IS Cq}]_{ESM}$; c) calculating a corrected delta Cq using the formula $[\text{NT Cq}-\text{IS Cq}]_{Target\ Gene}-[\text{NT Cq}-\text{IS Cq}]_{ESM}$; d) obtaining a target gene NT copy number by multiplying $2^{(-corrected\ delta\ Cq)}$ by the known number of input IS copies corresponding to the target gene in the reaction; and e) normalizing the target gene NT copy number to a reference gene loading control gene NT value.

Another particular embodiment provided herein provides a method to control for inter-experimental variation occurring during two-color RT-qPCR amplification comprising: a) providing one or more synthetic competitive internal standards (IS), wherein each IS is synthesized to correspond with a unique target gene or reference gene, and wherein known quantities of the one or more IS are formulated into an internal standards mixture (ISM); b) providing an external standards mixture (ESM) comprising: 1) one or more purified synthetic NT, wherein each NT is synthesized to correspond with a unique target gene or reference gene; and 2) one or more synthetic competitive internal standards (IS), wherein each IS is synthesized to correspond with a unique target gene or reference gene, wherein known quantities of each purified synthetic NT and IS are formulated into the ESM; c) while running a two-color RT-qPCR amplification to quantify a target gene using the ISM, simultaneously amplify two distinct concentrations of ESM, wherein the ESM comprises probes for the NT and IS being quantified; d) correcting a measured copy number for one or more target genes by: 1) calculating the difference in quantification cycle (Cq) between NT and IS for a target gene ($[\text{NT Cq}-\text{IS Cq}]_{Target\ Gene}$); 2) calculating an average difference in Cq between NT and IS of two concentrations of ESM (($[\text{NT Cq}-\text{IS Cq}]_{ESM\ Concentration\ 1}+[\text{NT Cq}-\text{IS Cq}]_{ESM\ Concentration\ 2})/2=[\text{NT Cq}-\text{IS Cq}]_{ESM}$); 3) calculating the corrected delta Cq using the formula $[\text{NT Cq}-\text{IS Cq}]_{Target\ Gene}-[\text{NT Cq}-\text{IS Cq}]_{ESM}$; 4) obtaining a target gene NT copy number by multiplying $2^{(-corrected\ delta\ Cq)}$ by the known number of input IS copies corresponding to the target gene in the reaction; and 5) normalizing the target gene NT copy number to a reference gene loading control gene NT value, wherein normalizing the target gene NT copy number to a reference gene loading control gene NT value controls for inter-experimental variation occurring during two-color RT-qPCR, as any variation in the observed $[\text{NT Cq}-\text{IS Cq}]_{ESM}$ relative to the expected value of 0 is attributable to the inter-experimental variation.

In another particular embodiment provided herein is a method, wherein the two-color RT-qPCR amplification is being done on cDNA originated from a sample having degraded RNA therein.

In another particular embodiment provided herein is a method, wherein the inter-experimental variation arises from variation in fluorescence specific activity.

In another particular embodiment provided herein is a method, wherein the inter-experimental variation arises from the RT-qPCR reaction being conducted on a different machine.

In another particular embodiment provided herein is a method, wherein the inter-experimental variation arises from variation in equipment and procedures between different laboratories.

Other systems, methods, features, and advantages of the present invention will be or will become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF THE DRAWINGS

The patent or application file may contain one or more drawings executed in color and/or one or more photographs. Copies of this patent or patent application publication with color drawing(s) and/or photograph(s) will be provided by the Patent Office upon request and payment of the necessary fee.

(FIGS. 5A-5B) Serial dilution of external standards mixture (ESM, 1/1 mixture of NT/IS) from $10^{-11}$M through $10^{-17}$M (triplicate measurements, with error bars). (FIGS. 5C-5D) NT dilution relative to constant IS from 1/1 NT/IS ($10^{-12}$M) down to 1/80 (NT/IS) (triplicate measurements with error bars). (FIGS. 5E-5F) IS dilution relative to constant NT from 1/1 NT/IS ($10^{-13}$M) down to 1/80-fold (one replicate). NT: native template. IS: internal standard.

FIGS. 7A, 7C, 7E, 7G: Linearity from 1/1 to 1/10-fold IS dilution. FIGS. 7B, 7D, 7F, 7H: Linearity from 1/1 to 1/80-fold IS dilution. 1/1, 1/2, 1/3, 1/4, 1/5, 1/6, 1/7, 1/8, 1/9, 1/10, 1/12, 1/14, 1/16, 1/18, 1/20, 1/24, 1/28, 1/32, 1/36, 1/40, 1/48, 1/56, 1/64, 1/72, and 1/80-fold dilutions of IS relative to constant NT were assessed (one replicate measurement). Auto Cq could not be generated for the 1/56, 1/64, 1/72, 1/80-fold IS dilutions of ACTB.

(FIG. 8A) pre-amplification. (FIG. 8B) no pre-amplification. The optimal PCR condition was assumed to be 20 μl reaction volume (2V), 800 nM of primers (1 Pm) and 200 nM of probes (1 Pb). Formalin-fixed, paraffin-embedded surgically removed, malignant sample 1(SM1) reverse transcribed with gene-specific primer was used. To test robustness, the volume was reduced by half, and/or doubled primer or probe concentration in each of the two conditions (pre-amp or no pre-amp).

(FIG. 10A) Quantification cycle (Cq) values of MYC IS, MYC NT, ACTB IS, ACTB NT. (FIG. 10B) Molecules of each gene and normalized value of MYC/$10^6$ ACTB molecules (triplicate measurements) analyzed in benign, non-FFPE lung cDNA reverse transcribed with gene specific primers. NT: native template. IS: internal standard. FFPE: formalin-fixed, paraffin-embedded. The asterisk (*) indicates that Cq values were undetermined by software.

(FIGS. 11A-11D) Effect of diluting labeled probe with unlabeled probe on measurement of MYC in benign, non-FFPE lung cDNA reverse transcribed with gene specific primers (triplicate measurements, with error bars). (FIGS. 11A-11B) NT labeled probe diluted with NT unlabeled probe. (FIGS. 11C-11D) IS labeled probe diluted with IS unlabeled probe. FFPE: formalin-fixed, paraffin-embedded. The asterisk (*) indicates that Cq values were undetermined by software.

FIG. 11E: Effect of inter-day variation in Cq threshold selection on measurement of MYC and ACTB in surgically removed formalin fixed paraffin embedded sample 8 (SM8). NT: native template. IS: internal standard.

FIG. 11F: External standards mixture (ESM) controls for inter-experimental variation in fluor signal or quantification cycle (Cq) selection. Effect of inter-day variation in threshold selection on measurement of ACTB in formalin fixed paraffin embedded sample 8 (SM8).

(FIG. 12A) lung cancer diagnostic test (LCDT) index values by diagnostic class. (FIG. 12B) receiver operator characteristic curve (ROC) of LCDT index.

(FIG. 14A) Total RNA extracted and RNA purity from surgically removed FFPE samples. (FIG. 14B) Total RNA extracted and RNA purity from fine needle aspirate FFPE samples.

DETAILED DESCRIPTION OF THE INVENTION

Figure 1A:
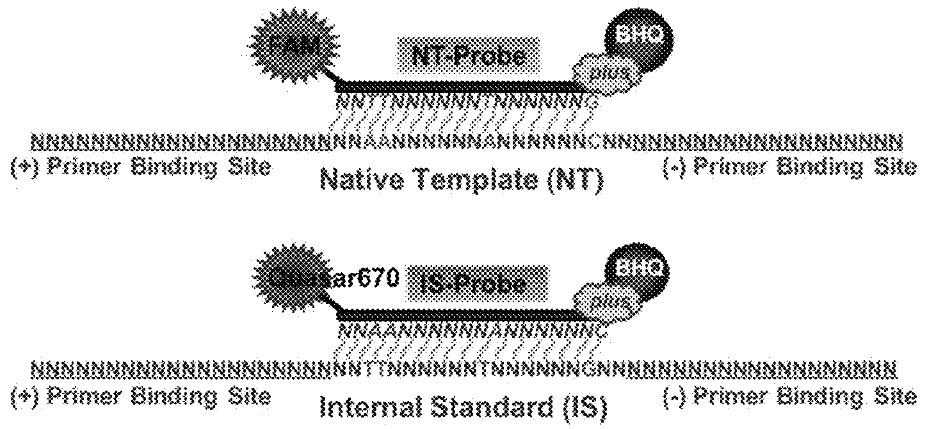
FIG. 1A: Depicted is a schematic illustration of the probe design. Native template (NT) binding hydrolysis probes were labeled with FAM. Internal standard (IS) binding hydrolysis probes were labeled with Quasar 670. For each gene, NT and IS had the same primer binding sites but there was a 4-6 bp difference in probe binding sites. Figure discloses SEQ ID NOS 25-28, respectively, in order of appearance.

Throughout this disclosure, various publications, patents and published patent specifications are referenced. The disclosures of these publications, patents and published patent specifications are hereby incorporated by reference into the present disclosure to more fully describe the state of the art to which this invention pertains.

Described herein are methods for assessing amounts of nucleic acid in a formalin fixed paraffin embedded (FFPE) sample. In some embodiments, the method allows measurement of small amounts of nucleic acid, for example, where the nucleic acid is extractable only in low amounts in a specimen, where small amounts of the nucleic acid remain intact and/or where small amounts of a specimen are provided.

DEFINITIONS

As used herein, "sample" can refer to material collected for analysis, e.g., a swab of culture, a pinch of tissue, a biopsy extraction, a vial of a bodily fluid e.g., saliva, blood and/or urine, etc. that is taken for research, diagnostic or other purposes from any biological entity.

Sample can also refer to a biopsy extraction that is typically formalin fixed and paraffin embedded. Sample can also refer to amounts typically collected in biopsies, e.g., endoscopic biopsies (using brush and/or forceps), needle aspirate biopsies (including fine needle aspirate biopsies), as well as amounts provided in sorted cell populations (e.g., flow-sorted cell populations) and/or micro-dissected materials (e.g., laser captured micro-dissected tissues). For example, biopsies of suspected cancerous lesions in the lung, breast, prostate, thyroid, and pancreas, commonly are done by fine needle aspirate (FNA) biopsy, bone marrow is also obtained by biopsy, and tissues of the brain, developing embryo, and animal models may be obtained by laser captured micro-dissected samples.

In some embodiments, the sample collected may comprise less than about 100,000 cells, less than about 10,000 cells, less than about 5,000 cells, less than about 1,000 cells, less than about 500 cells, less than about 100 cells, less than about 50 cells, or less than about 10 cells.

In some embodiments, assessing, evaluating and/or measuring a nucleic acid can refer to providing a measure of the amount of a nucleic acid in a sample, e.g., to determine the level of expression of a gene. In some embodiments, providing a measure of an amount refers to detecting a presence or absence of the nucleic acid of interest. In some embodiments, providing a measure of an amount can refer to quantifying an amount of a nucleic acid, e.g., providing a measure of concentration or degree of the amount of the nucleic acid present. In some embodiments, providing a measure of the amount of nucleic acid refer to enumerating the amount of the nucleic acid, e.g., indicating a number of molecules of the nucleic acid present in a sample. The "nucleic acid of interest" may be referred to as a "target" nucleic acid, and/or a "gene of interest," e.g., a gene being evaluated, may be referred to as a target gene. The number of molecules of a nucleic acid can also be referred to as the number of copies of the nucleic acid found in a sample and/or specimen.

"Biological entity" as used herein can refer to any entity capable of harboring a nucleic acid, including any species, e.g., a virus, a cell, a tissue, an in vitro culture, a plant, an animal, a subject participating in a clinical trial, and/or a subject being diagnosed or treated for a disease or condition.

As used herein, "nucleic acid" can refer to a polymeric form of nucleotides and/or nucleotide-like molecules of any length. In certain embodiments, the nucleic acid can serve as a template for synthesis of a complementary nucleic acid, e.g., by base-complementary incorporation of nucleotide units. For example, a nucleic acid can comprise naturally occurring DNA, e.g., genomic DNA; RNA, e.g., mRNA, and/or can comprise a synthetic molecule, including but not limited to cDNA and recombinant molecules generated in any manner. For example, the nucleic acid can be generated from chemical synthesis, reverse transcription, DNA replication or a combination of these generating methods. The linkage between the subunits can be provided by phosphates, phosphonates, phosphoramidates, phosphorothioates, or the like, or by nonphosphate groups, such as, but not limited to peptide-type linkages utilized in peptide nucleic acids (PNAs). The linking groups can be chiral or achiral. The polynucleotides can have any three-dimensional structure, encompassing single-stranded, double-stranded, and triple helical molecules that can be, e.g., DNA, RNA, or hybrid DNA/RNA molecules.

A nucleotide-like molecule can refer to a structural moiety that can act substantially like a nucleotide. For example, exhibiting base complementarity with one or more of the bases that occur in DNA or RNA and/or being capable of base-complementary incorporation. The terms "polynucleotide," "polynucleotide molecule," "nucleic acid molecule," "polynucleotide sequence" and "nucleic acid sequence," can be used interchangeably with "nucleic acid" herein. In some specific embodiments, the nucleic acid to be measured may comprise a sequence corresponding to a specific gene.

The term "native template" as used herein can refer to nucleic acid obtained directly or indirectly from a specimen that can serve as a template for amplification. For example, it may refer to cDNA molecules, corresponding to a gene whose expression is to be measured, where the cDNA is amplified and quantified.

The term "primer" generally refers to a nucleic acid capable of acting as a point of initiation of synthesis along a complementary strand when conditions are suitable for synthesis of a primer extension product.

The term "fluorometric hydrolysis probe" generally refers to a fluorescently labeled probe that takes advantage of the 5'-nuclease activity present in the thermostable Taq polymerase enzyme typically used in the PCR reaction. The hydrolysis probe may be labeled with a fluorescent detector dye such as FAM or Quasar 670, and an acceptor dye or quencher. In general, the fluorescent dye is covalently attached to the 5' end of the probe and the quencher is attached to the 3' end of the probe, and when the probe is intact, the fluorescence of the detector dye is quenched by fluorescence resonance energy transfer (FRET). The probe anneals downstream of one of the primers that defines one end of the target nucleic acid in a PCR reaction. Using the polymerase activity of the Taq enzyme, amplification of the target nucleic acid is directed by one primer that is upstream of the probe and a second primer that is downstream of the probe but anneals to the opposite strand of the target nucleic acid. As the upstream primer is extended, the Taq polymerase reaches the region where the labeled probe is annealed, recognizes the probe-template hybrid as a substrate, and hydrolyzes phosphodiester bonds of the probe.

The hydrolysis reaction irrevocably releases the quenching effect of the quencher dye on the reporter dye, thus resulting in increasing detector fluorescence with each successive PCR cycle.

The term "fluorescent dye," as used herein, generally refers to any dye that emits electromagnetic radiation of longer wavelength by a fluorescent mechanism upon irradiation by a source of electromagnetic radiation, such as a lamp, a photodiode, or a laser.

General Description of Invention

In one embodiment, described herein is a kit that is useful in molecular diagnostic testing a sample. The kit generally includes: a) synthetic competitive internal standards (IS), wherein known quantities of each IS are formulated into an internal standards mixture (ISM); b) an external standards mixture (ESM) comprising 1) purified synthetic NT, and 2) synthetic competitive internal standards (IS), wherein known quantities of each purified synthetic NT and IS are formulated into the ESM; c) pairs of gene-specific primers (GSP) specific to genes ACTB (forward primer: SEQ ID NO: 1; reverse primer: SEQ ID NO: 2), CDKN1A (forward primer: SEQ ID NO: 3; reverse primer: SEQ ID NO: 4), MYC (forward primer: SEQ ID NO: 5; reverse primer: SEQ ID NO: 6), and E2F1 (forward primer: SEQ ID NO: 7; reverse primer: SEQ ID NO: 8); and d) sequence-specific fluorometric hydrolysis probes, individual fluorometric hydrolysis probes comprising one each of: SEQ ID NO: 9; SEQ ID NO: 10; SEQ ID NO: 11; SEQ ID NO: 12; SEQ ID NO: 13; SEQ ID NO: 14; SEQ ID NO: 15; or SEQ ID NO: 16; wherein all fluorometric hydrolysis probes are labeled with a fluorescent reporter.

In another particular embodiment provided herein is a kit wherein SEQ ID NO: 9, SEQ ID NO: 11, SEQ ID NO: 13, and SEQ ID NO: 15 are labeled with FAM, and SEQ ID NO: 10, SEQ ID NO: 12, SEQ ID NO: 14, and SEQ ID NO: 16 are labeled with Quasar 670.

Another particular embodiment provided herein provides a method for using a kit described herein, comprising the steps of: a) extracting RNA from a sample; b) reverse-transcribing (RT) the RNA extracted from the sample; c) pre-amplifying cDNA generated by the RT of the RNA extracted from the sample along with the ISM, wherein the pre-amplification of the cDNA and ISM is done by polymerase chain reaction (PCR) using the pairs of GSP specific to the genes; d) performing a second round of PCR amplification for genes, wherein a reaction mixture for a single gene comprises: 1) a dilution of the pre-amplified cDNA and ISM; 2) a primer mixture comprising the pairs of GSP corresponding to the genes; and 3) fluorometric hydrolysis probes specific for the single gene NT and corresponding IS; e) along with the second round of PCR amplification, for each gene, simultaneously performing PCR amplification on two distinct concentrations of the ESM, wherein each distinct concentration of ESM further comprises the same fluorometric hydrolysis probes specific for the single gene NT and corresponding IS of step d) 3); and f) quantifying the copy number for target genes CDKN1A, MYC, and E2F1.

In a particular embodiment described herein is a kit for use in molecular diagnostic testing of lung cancer in a sample, comprising a) synthetic competitive internal standards (IS), individual IS comprising one each of: SEQ ID NO: 18; SEQ ID NO: 20; SEQ ID NO: 22; or SEQ ID NO: 24, wherein known quantities of each IS are formulated into an internal standards mixture (ISM); b) an external standards mixture (ESM) comprising 1) purified synthetic NT, individual NT comprising one each of: SEQ ID NO: 17; SEQ ID NO: 19; SEQ ID NO: 21; or SEQ ID NO:23; and 2) synthetic competitive internal standards (IS), individual IS comprising one each of: SEQ ID NO: 18; SEQ ID NO: 20; SEQ ID NO: 22; or SEQ ID NO: 24, wherein known quantities of each purified synthetic NT and IS are formulated into the ESM at a ratio of 1:1; c) pairs of gene-specific primers (GSP) specific to genes ACTB (forward primer: SEQ ID NO: 1; reverse primer: SEQ ID NO: 2), CDKN1A (forward primer: SEQ ID NO: 3; reverse primer: SEQ ID NO: 4), MYC (forward primer: SEQ ID NO: 5; reverse primer: SEQ ID NO: 6), and E2F1 (forward primer: SEQ ID NO: 7; reverse primer: SEQ ID NO: 8); and d) sequence-specific fluorometric hydrolysis probes, individual fluorometric hydrolysis probes comprising one each of: SEQ ID NO: 9; SEQ ID NO: 10; SEQ ID NO: 11; SEQ ID NO: 12; SEQ ID NO: 13; SEQ ID NO: 14; SEQ ID NO: 15; or SEQ ID NO: 16; wherein all fluorometric hydrolysis probes are labeled with a fluorescent reporter.

In another particular embodiment provided herein is a kit wherein SEQ ID NO: 9, SEQ ID NO: 11, SEQ ID NO: 13, and SEQ ID NO: 15 are labeled with FAM, and SEQ ID NO: 10, SEQ ID NO: 12, SEQ ID NO: 14, and SEQ ID NO: 16 are labeled with Quasar 670.

Another particular embodiment provided herein provides a method for using a kit described herein, comprising the steps of: a) extracting RNA from a sample; b) reverse-transcribing (RT) the RNA extracted from the sample; c) pre-amplifying cDNA generated by the RT of the RNA extracted from the sample along with the ISM, wherein the pre-amplification of the cDNA and ISM is done by polymerase chain reaction (PCR) using the pairs of GSP specific to the genes ACTB, CDKN1A, MYC, and E2F1; d) performing a second round of PCR amplification for genes ACTB, CDKN1A, MYC, and E2F1, wherein a reaction mixture for a single gene comprises: 1) a dilution of the pre-amplified cDNA and ISM; 2) a primer mixture comprising the pairs of GSP corresponding to genes ACTB, CDKN1A, MYC, and E2F1; and 3) fluorometric hydrolysis probes specific for the single gene NT and corresponding IS; e) along with the second round of PCR amplification, for each gene, simultaneously performing PCR amplification on two distinct concentrations of the ESM, wherein each distinct concentration of ESM further comprises the same fluorometric hydrolysis probes specific for the single gene NT and corresponding IS of step d) 3); and f) quantifying the copy number for target genes CDKN1A, MYC, and E2F1.

In another particular embodiment provided herein is a method for using a kit described herein, wherein the two distinct concentrations of ESM differ by at least one order of magnitude.

In another particular embodiment provided herein is a method for using a kit described herein, wherein the two distinct concentrations of ESM are $10^{-13}$ M NT/$10^{-13}$ M IS and $10^{-14}$ M NT/$10^{-14}$ M IS.

In another particular embodiment provided herein is a method for using a kit described herein, wherein the step of quantifying the copy number for each target gene comprises the steps of: a) calculating the difference in quantification cycle (Cq) between the NT and IS for a target gene using the formula $[\text{NT Cq}-\text{IS Cq}]_{Target\ Gene}$; b) calculating an average difference in Cq between the NT and IS of two concentrations of ESM using the formula $([\text{NT Cq}-\text{IS Cq}]_{ESM\ Concentration\ 1}+[\text{NT Cq}-\text{IS Cq}]_{ESM\ Concentration\ 2})/2=[\text{NT Cq}-\text{IS Cq}]_{ESM}$; c) calculating a corrected delta Cq using the formula $[\text{NT Cq}-\text{IS Cq}]_{Target\ Gene}-[\text{NT Cq}-\text{IS Cq}]_{ESM}$; d) obtaining a target gene NT copy number by multiplying $2^{(-corrected\ delta\ Cq)}$ by a known number of input IS copies corresponding to the target gene in the reaction; and e) normalizing the target gene NT copy number to an ACTB gene loading control NT value.

In another particular embodiment provided herein is a method described herein, wherein the samples comprise material having degraded RNA therein.

In another particular embodiment provided herein is a method described herein, wherein the samples comprise formalin fixed paraffin embedded (FFPE) samples.

In another particular embodiment provided herein is a method described herein, wherein the samples comprise fresh-frozen samples.

In a particular embodiment described herein is a kit for use in A kit for use in molecular diagnostic testing of a sample comprising: a) one or more synthetic competitive internal standards (IS), wherein each IS is synthesized to correspond with a unique target gene or reference gene, wherein an IS probe binding site has a 4-6 bp difference than that of a native template (NT), and wherein known quantities of the one or more IS are formulated into an internal standards mixture (ISM); b) an external standards mixture (ESM) comprising: 1) one or more purified synthetic NT, wherein each NT is synthesized to correspond with a unique target gene or reference gene; and 2) one or more synthetic competitive internal standards (IS), wherein each IS is synthesized to correspond with a unique target gene or reference gene, wherein known quantities of each purified synthetic NT and IS are formulated into the ESM at a ratio of 1:1; c) one or more pairs of gene-specific primers (GSP), wherein each pair of GSP is specific for a unique target gene or reference gene, and is designed to amplify a PCR product having a product size of approximately 60-80 base pairs and span introns/exon splice junctions of the unique target gene or reference gene; and d) at least one pair of fluorometric hydrolysis probes, wherein each pair of fluorometric probes is specific for a particular target gene or reference gene, and comprises a first fluorometric hydrolysis probe that is sequence-specific for an NT probe binding site and is labeled with a first fluorescent reporter, and a second fluorometric hydrolysis probe that is sequence specific for an IS probe binding site of an IS corresponding to the NT against which the first fluorometric hydrolysis probe is sequence-specific for, and is labeled with a second fluorescent reporter.

In another particular embodiment described herein is a kit for use in molecular diagnostic testing of a sample, wherein the first fluorometric hydrolysis probe sequence-specific for the NT probe binding site is labeled with FAM, and the second fluorometric hydrolysis probe sequence specific for the IS probe binding site is labeled with Quasar 670.

Another particular embodiment provided herein provides a method for using a kit described herein, comprising the steps of: a) extracting RNA from the sample; b) reverse-transcribing (RT) the RNA extracted from the sample; c) pre-amplifying cDNA generated by the RT of the RNA extracted from the sample along with ISM including IS for each target gene or reference gene, wherein the pre-amplification of the cDNA and ISM is done by polymerase chain reaction (PCR) using the pairs of GSP specific to each target gene or reference gene; d) performing a second round of PCR amplification for each target gene and at least one reference gene, wherein a reaction mixture for a single target gene or reference gene comprises: 1) a dilution of the pre-amplified cDNA and ISM; 2) a primer mixture comprising the one or more pairs of GSP; and 3) one pair of fluorometric hydrolysis probes, specific for a single target gene or reference gene and its corresponding IS; e) along with the second round of PCR amplification, for each target gene or reference gene, simultaneously performing a PCR amplification on two distinct concentrations of the ESM containing the same pair of fluorometric hydrolysis probes used in step d) 3); and f) quantifying the copy number for each target gene.

In another particular embodiment provided herein is a method for using a kit described herein, wherein the step of quantifying the copy number for each target gene comprises the steps of: a) calculating the difference in quantification cycle (Cq) between the NT and IS for a target gene using the formula$[\text{NT Cq}-\text{IS Cq}]_{Target\ Gene}$; b) calculating an average difference in Cq between the NT and IS of two concentrations of ESM using the formula $([\text{NT Cq}-\text{IS Cq}]_{ESM\ Concentration\ 1}+[\text{NT Cq}-\text{IS Cq}]_{ESM\ Concentration\ 2})/2=[\text{NT Cq}-\text{IS Cq}]_{ESM}$; c) calculating a corrected delta Cq using the formula $[\text{NT Cq}-\text{IS Cq}]_{Target\ Gene}-[\text{NT Cq}-\text{IS Cq}]_{ESM}$; d) obtaining a target gene NT copy number by multiplying $2^{(-corrected\ delta\ Cq)}$ by the known number of input IS copies corresponding to the target gene in the reaction; and e) normalizing the target gene NT copy number to a reference gene loading control gene NT value.

Another particular embodiment provided herein provides a method to control for inter-experimental variation occurring during two-color RT-qPCR amplification comprising: a) providing one or more synthetic competitive internal standards (IS), wherein each IS is synthesized to correspond with a unique target gene or reference gene, and wherein known quantities of the one or more IS are formulated into an internal standards mixture (ISM); b) providing an external standards mixture (ESM) comprising: 1) one or more purified synthetic NT, wherein each NT is synthesized to correspond with a unique target gene or reference gene; and 2) one or more synthetic competitive internal standards (IS), wherein each IS is synthesized to correspond with a unique target gene or reference gene, wherein known quantities of each purified synthetic NT and IS are formulated into the ESM; c) while running a two-color RT-qPCR amplification to quantify a target gene using the ISM, simultaneously amplify two distinct concentrations of ESM, wherein the ESM comprises probes for the NT and IS being quantified; d) correcting a measured copy number for one or more target genes by: 1) calculating the difference in quantification cycle (Cq) between NT and IS for a target gene ($[\text{NT Cq}-\text{IS Cq}]_{Target\ Gene}$); 2) calculating an average difference in Cq between NT and IS of two concentrations of ESM (($[\text{NT Cq}-\text{IS Cq}]_{ESM\ Concentration\ 1}+[\text{NT Cq}-\text{IS Cq}]_{ESM\ Concentration\ 2})/2=[\text{NT Cq}-\text{IS Cq}]_{ESM}$); 3) calculating the corrected delta Cq using the formula $[\text{NT Cq}-\text{IS Cq}]_{Target\ Gene}-[\text{NT Cq}-\text{IS Cq}]_{ESM}$; 4) obtaining a target gene NT copy number by multiplying $2^{(-corrected\ delta\ Cq)}$ by own number of input IS copies corresponding to the target gene in the reaction; and 5) normalizing the target gene NT copy number to a reference gene loading control gene NT value, wherein normalizing the target gene NT copy number to a reference gene loading control gene NT value controls for inter-experimental variation occurring during two-color RT-qPCR, as any variation in the observed $[\text{NT Cq}-\text{IS Cq}]_{ESM}$ relative to the expected value of 0 is attributable to the inter-experimental variation.

In another particular embodiment provided herein is a method, wherein the two-color RT-qPCR amplification is being done on cDNA originated from a sample having degraded RNA therein.

In another particular embodiment provided herein is a method, wherein the inter-experimental variation arises from variation in fluorescence specific activity.

In another particular embodiment provided herein is a method, wherein the inter-experimental variation arises from the RT-qPCR reaction being conducted on a different machine.

In another particular embodiment provided herein is a method, wherein the inter-experimental variation arises from variation in equipment and procedures between different laboratories It is to be understood that the presently described kits and methods are also useful to also to include detection of PCR products by melting curve analysis (i.e., SNAQ). For example, see U.S. Pat. No. 7,527,930, issued May 5, 2009, for "Compositions And Methods Of Use Of Standardized Mixtures For Determining An Amount Of A Nucleic Acid" which is expressly incorporated herein by reference, and which describes a multiplex two-step technology that includes a Standardized NanoArray PCR (SNAQ) platform, and also describes use of standardized mixtures of internal standards.

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. All publications, including patents and non-patent literature, referred to in this specification are expressly incorporated by reference. The following examples are intended to illustrate certain preferred embodiments of the invention and should not be interpreted to limit the scope of the invention as defined in the claims, unless so specified. The value of the present invention can thus be seen by reference to the Examples herein.

EXAMPLES

Materials and Methods

Ethics Statement: Twenty archived surgical FFPE lung tissues that had been processed according to the standard University of Toledo Medical Center (UTMC) Department of Pathology practice were obtained for this study under UTMC IRB #107790. Each FFPE sample was assigned a non-identifying number by the pathologist and transferred to the research laboratory. The link between the non-identifying number and identifying information was destroyed by the pathologist immediately following sample transfer.

FFPE Sample Preparation: Microtome sections (10 micrometer thickness) were obtained from each sample. Six strips per sample (1 strip=4 sections) were obtained, and each strip was put in one 1.5 ml micro-centrifuge tube for RNA extraction. Therefore, 24 sections (240 micrometers) of each sample block were collected for RNA extraction.

RNA Extraction and Reverse Transcription: RNA was extracted from the surgical FFPE samples using the RNeasy® FFPE Kit (Qiagen, Valencia, Calif.). RNA was treated with DNase in the RNeasy® FFPE Kit RNA extraction protocol in order to minimize the effect of contaminating genomic DNA. RNA purity and integrity were assessed using absorbance at 260/280 nm ratios and RNA integrity number (RIN) scores as detected on the Agilent 2100 Bioanalyzer (Agilent Technologies, Santa Clara, Calif.). The effect of different conditions on reverse transcription (RT) efficiency, including priming with random hexamer primers (RHP) or GSP and use of 1 or 5 μg of RNA in the 30 μl RT reaction, was assessed with three FFPE samples. A previously described test using the External RNA Control Consortium (ERCC) standards was used to measure RT efficiency. After completion of these studies, optimal RT conditions were selected consisting of a 30 μl RT reaction with 1 μg of RNA, gene-specific RT primer (the PCR reverse primer) (3 μM), and SuperScript III First Strand Synthesis System (Life Technologies, Grand Island, N.Y.).

Primer Design and Testing of Efficiency and Specificity: For each gene (MYC, E2F1, CDKN1A and ACTB) primers were designed to 1) amplify the shortest possible PCR product size (60-80 base pairs) and 2) span intron/exon splice junctions to minimize the effect of residual genomic DNA contamination (Table 1).

Each candidate primer pair was assessed for efficiency in a serially diluted mixture of H23 cell line cDNA and ISM using endpoint PCR. After 35 PCR cycles, products were electrophoretically separated on an Agilent 2100 Bioanalyzer (Agilent Technologies, Santa Clara, Calif.), the electropherogram was inspected for presence or absence of non-specific products, and appropriately sized peaks were quantified by densitometry.

Design of Probes and IS Templates: For each gene target, after native template (NT) primers with sufficient efficiency and specificity were identified, real-time PCR assays using fluorometric hydrolysis probes were developed. First, a probe for the NT was designed followed by the design of an IS probe for the same DNA region but with 4-6 base pair alterations from the NT probe sequence. An IS template with corresponding alterations was synthesized as described in the synthesis and purification of standards section below. Use of multiple base changes in the IS probe ensured specificity of NT probe (FAM labeled) for the NT and IS probe (Quasar 670 labeled) for the IS. Probes with a fluorescent label at the 5' end and a Black Hole Quencher at the 3' end (BHQplus, Biosearch Technologies, Novato, Calif.) were designed using real-time design software from Biosearch Technologies (FIG. 1A, Table 1).

Synthesis and Purification of Standards: For each gene, an NT (to be used in the ESM) was synthesized and an IS was obtained via commercial vendor (Life Technologies, Grand Island, N.Y.). The products of such syntheses are single-stranded and contain a significant fraction of incompletely synthesized (less than full-length) molecules. Thus, each synthesized NT or IS was PCR-amplified with GSP to generate completely synthesized, double-stranded nucleic acid templates. This was followed by electrophoretic separation of the PCR products on agarose gel, selection of the correct size band, and purification from agarose using QIAX II gel extraction kit (Qiagen, Valencia, Calif.) (Table 1).

Probe Specificity Test: Specificity of each probe was tested by including it in PCR assays containing the synthetic NT or IS serially diluted from $10^{-11}$M to $10^{-15}$M. For each probe, at each NT or IS dilution, the signal (Cq value: quantification cycle) observed with amplification in the presence of the non-homologous template was compared to Cq value observed with amplification in the presence of the homologous template. The non-specific binding rate was calculated using $2^{(-delta\ Cq)}$ (delta Cq=non-homologous template Cq−homologous template Cq) at each dilution. If, at any concentration, the number of input non-homologous molecules detected by the probe was more than 10% of the number of homologous molecules detected, then the probe was re-designed.

TABLE 1

Sequences of primers, probes, and standard templates for two-color fluorometric real-time measurement.

Primer sequences

| Gene | Location | GenBank Acession no. | Primer | Sequence (5'- 3') | Size |
|---|---|---|---|---|---|
| ACTB | Exon 4, 5 | NM_001101.3 | Forward | GCCCTGAGGCACTCTTCCAG (SEQ ID NO: 1) | 20 bp |
| | | | Reverse | TTTCGTGGATGCCACAGGAC (SEQ ID NO: 2) | 20 bp |
| CDKN1A | Exon 5, 6 | NM_000389.4 | Forward | CCTGGAGACTCTCAGGGTCG (SEQ ID NO: 3) | 20 bp |
| | | | Reverse | GCGTTTGGAGTGGTAGAAAT (SEQ ID NO: 4) | 20 bp |
| MYC | Exon 1, 2 | NM_002467.4 | Forward | AGCTGCTTAGACGCTGGATT (SEQ ID NO: 5) | 20 bp |
| | | | Reverse | CTAACGTTGAGGGGCATCGT (SEQ ID NO: 6) | 20 bp |
| E2F1 | Exon 5, 6 | NM_005225.2 | Forward | CTCCTCAGGGCACAGGAA (SEQ ID NO: 7) | 18 bp |
| | | | Reverse | CGTGGACTCTTCGGAGAACTTTC (SEQ ID NO: 8) | 23 bp |

Probe sequences

| Gene | Probe | Modification 5' | 3' | Sequence (5'- 3') | Size |
|---|---|---|---|---|---|
| ACTB | NT probe | FAM | BHQ plus-1 | CCTTCCTTCCTGGGCATG (SEQ ID NO: 9) | 18 bp |
| | IS probe | Quasar 670 | BHQ plus-2 | CC***AA***CCTTCC***A***GGGCAT***C*** (SEQ ID NO: 10) | 18 bp |
| CDKN1A | NT probe | FAM | BHQ plus-1 | AAACGGCGGCAGACCAGC (SEQ ID NO: 11) | 18 bp |
| | IS probe | Quasar 670 | BHQ plus-2 | ***TT***ACGGCGG***GT***GACCA***C*** (SEQ ID NO: 12) | 17 bp |
| MYC | NT probe | FAM | BHQ plus-1 | TAGTGGAAAACCAGCAGCCT (SEQ ID NO: 13) | 20 bp |
| | IS probe | Quasar 670 | BHQ plus-2 | ***AT***GTGGAAA***T***CC***T***GCAGC***GA*** (SEQ ID NO: 14) | 20 bp |
| E2F1 | NT probe | FAM | BHQ plus-1 | CATCGATCGGGCCTTGTT (SEQ ID NO: 15) | 18 bp |
| | IS probe | Quasar 670 | BHQ plus-2 | ***TTC***CGATCG***T***GCCTT***CTA*** (SEQ ID NO: 16) | 18 bp |

NT and IS sequences

| Gene | Template | Sequence (5'- 3') | Size |
|---|---|---|---|
| ACTB | NT | GCCCTGAGGCACTCTTCCAGCCTTCCTTCCTGGGCATGGAGTCCTGTGGCATCCACGAAA (SEQ ID NO: 17) | 60 bp |
| | IS | GCCCTGAGGCACTCTTCCAGCC***AA***CCTTCC***A***GGGCAT***C***GAGTCCTGTGGCATCCACGAAA (SEQ ID NO: 18) | 60 bp |
| CDKN1A | NT | CCTGGAGACTCTCAGGGTCGAAAACGGCGGCAGACCAGCATGACAGATTTCTACCACTCCAAACGC (SEQ ID NO: 19) | 66 bp |
| | IS | CCTGGAGACTCTCAGGGTCGA***TT***ACGGCGG***GT***GACCA***C***CATGACAGATTTCTACCACTCCAAACGC (SEQ ID NO: 20) | 66 bp |
| MYC | NT | AGCTGCTTAGACGCTGGATTTTTTTCGGGTAGTGGAAAACCAGCAGCCTCCCGCGACGATGCCCCTCAACGTTAG (SEQ ID NO: 21) | 75 bp |
| | IS | AGCTGCTTAGACGCTGGATTTTTTTCGGG***AT***GTGGAAA***T***CC***T***GCAGC***GA***CCCGCGACGATGCCCCTCAACGTTAG (SEQ ID NO: 22) | 75 bp |
| E2F1 | NT | CTCCTCAGGGCACAGGAAAACATCGATCGGGCCTTGTTTGCTCTTAAGGGAGATCTGAAAGTTCTCCGAAGAGTCCACG (SEQ ID NO: 23) | 79 bp |
| | IS | CTCCTCAGGGCACAGGAAAA***TTC***CGATCG***T***GCCTT***CTA***TGCTCTTAAGGGAGATCTGAAAGTTCTCCGAAGAGTCCACG (SEQ ID NO: 24) | 79 bp |

Preparation of Internal Standards Mixture (ISM): Known quantities of the IS for each gene were combined into an ISM. Use of the ISM rather than individual IS in each experiment minimized inter-experimental variation as described in Table 2. Six different ISM were prepared (ISM A-F) containing different concentrations of target gene IS mixture (MYC, E2F1, CDKN1A) relative to the reference gene (ACTB) IS.

TABLE 2

| ISM composition | | |
|---|---|---|
| ISM (M) | ACTB IS molecules/ reaction | Target Gene IS molecules/ reaction |
| A(−12/−11) | 600000 | 6000000 |
| B(−12/−12) | 600000 | 600000 |
| C(−12/−13) | 600000 | 60000 |
| D(−12/−14) | 600000 | 6000 |
| E(−12/−15) | 600000 | 600 |
| F(−12/−16) | 600000 | 60 |

External Standards Mixture (ESM): Known quantities of purified synthetic NT and IS for each gene were combined into an ESM. The ESM was used to control for inter-experimental variation resulting from 1) instability or intensity differences of one fluor relative to the other and 2) software selection of Cq. A stock ESM with $10^{-11}$M NT/$10^{-11}$M IS was prepared, and then diluted to two working concentrations of $10^{-13}$M NT/$10^{-13}$M IS and $10^{-14}$M NT/$10^{-14}$M IS. Each of these two ESM concentrations was measured in each experiment and for each gene the average measured Cq difference [NT Cq−IS Cq] from the two ESM was used to correct the [NT Cq−IS Cq] value measured in each unknown sample (Table 3, FIG. 2).

Pre-Amplification (1st Round PCR): The pre-amplification reaction for each sample was prepared in a 20 μl volume and included 1) 2 μl primer mixture (ACTB, MYC, E2F1, CDKN1A) with concentration of each primer at 800 nM (final concentration of each primer in PCR of 80 nM), 2) 1 μl cDNA sample, 3) 1 μl ISM, and 4) 10 μl TaqMan Universal Master Mix II (No UNG: Uracil N-Glycosylase, Life Technologies, Grand Island, N.Y.) with 6 μl RNase-free water. Probes were not used in the pre-amplification. Cycle parameters were 95° C. for 10 min then 18 cycles at 95° C. for 15 s and 60° C. for 1 min. The ABI 7500 Fast real-time PCR system was used with standard mode (software v2.0.6, Life Technologies).

Figure 1B:
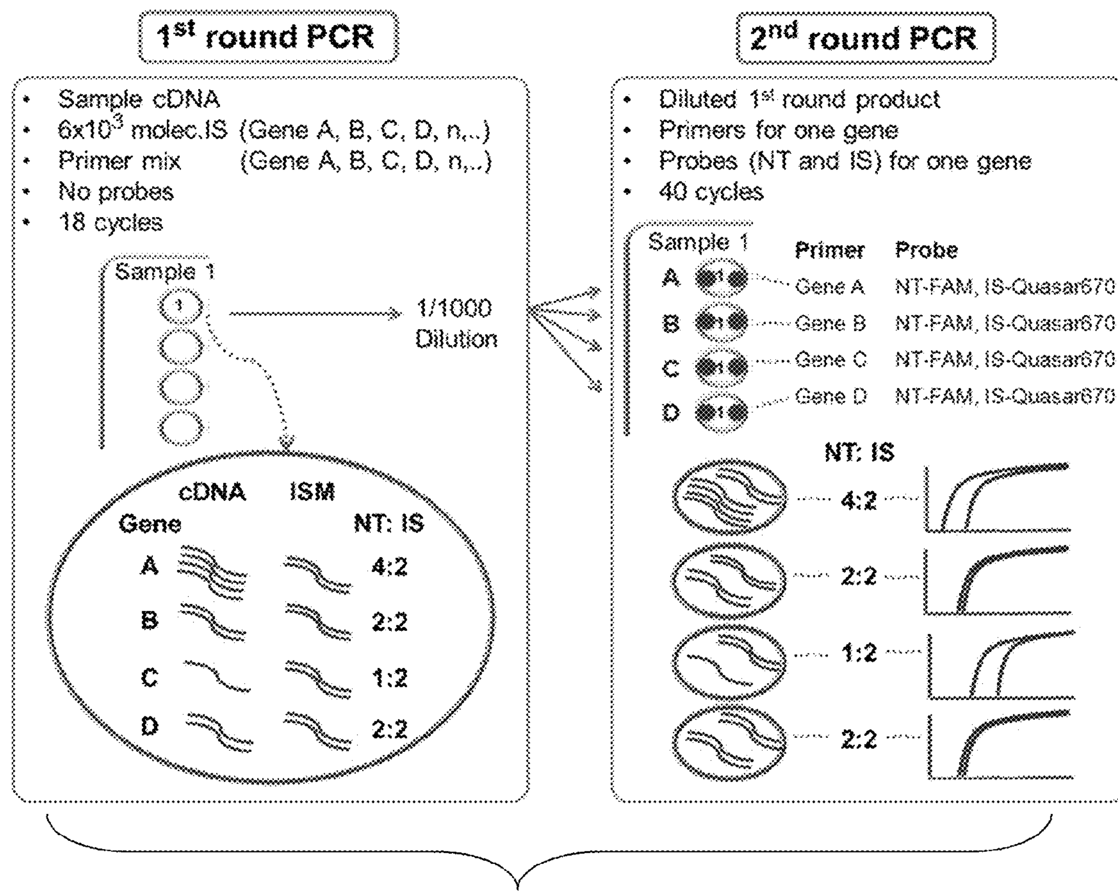
FIG. 1B: Depicted is a schematic illustration of the pre-amplification PCR. Varying concentrations of internal standards mixture (ISM) relative to cDNA were used to ensure that NT:IS ratio was >1:10 and <10:1.
Figure 2:
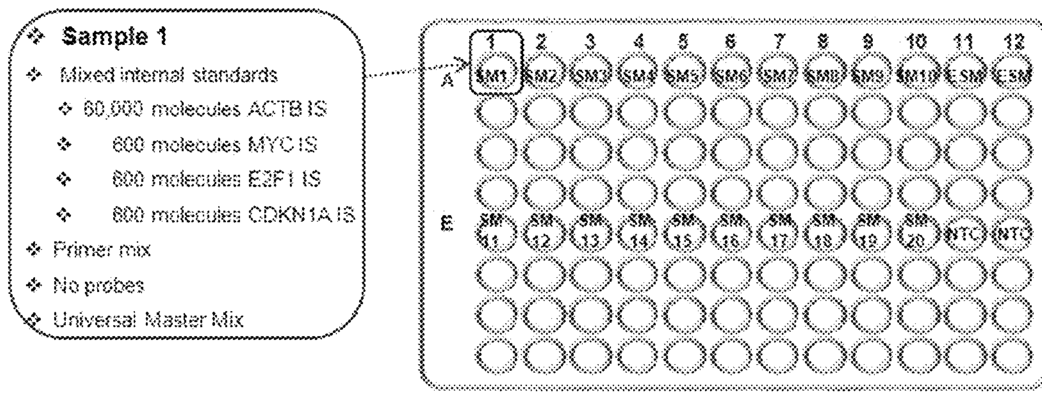
FIG. 2: Schematic plot of experiment set up for a 96 well plate. After dilution of pre-amplified PCR product containing cDNA and ISM, each sample was distributed for $2^{nd}$ amplification for each gene measurement with each primer and probe in individual wells. ISM C(−13/−15) was presented in the figure as an example containing ACTB $10^{-13}$ M/target gene $10^{-15}$ M corresponding to ACTB 60000/target gene 600 molecules. Two external standards ($10^{-13}$ M NT/IS and $10^{-14}$M NT/IS) PCR amplification plots were presented in one plot. Green (NT) and red (IS). Note: SM, surgically removed sample; ISM, internal standards mixture; ESM, external standards mixture.
Figure 2:
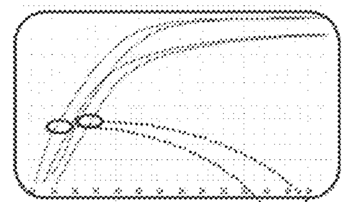
Figure 2:
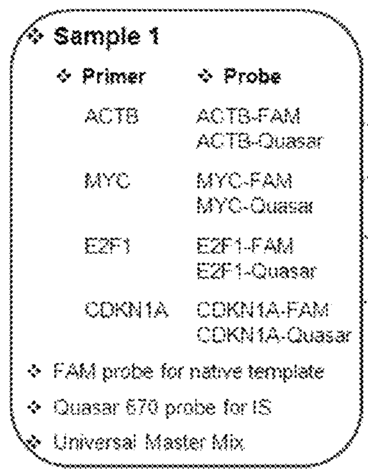

Second-Round PCR: Pre-amplified PCR products were diluted 1000-fold with TE buffer. A 20 μl reaction was prepared for each gene with 1) 1 μl of diluted pre-amplified product, 2) 2 μl of a primer mixture containing each primer for each gene at 8 μM (final concentration of each primer, 800 nM), 3) 2 μl of 2 μM NT probe and 2 μl of 2 μM IS probe (final concentration of each probe, 200 nM), 4) 10 μl TaqMan Universal Master Mix II (No UNG) with 3 μl RNase-free water, and subjected to 40 cycles of PCR using the same cycle parameters as in the pre-amplification. Automatic threshold was used to determine Cq values (FIG. 1B, FIG. 2).

TABLE 3

Example of MYC/$10^6$ ACTB calculation in Sample SM1

| Sample | ISM (M) | NT Cq | IS Cq | ΔCq | Ave. of ESM (NT Cq − IS Cq) | Corrected ΔCq | $2^{(-\Delta Cq)}$ | IS Molec. | Target Molec. | MYC/$10^6$ ACTB |
|---|---|---|---|---|---|---|---|---|---|---|
| ESM $10^{-13}$ M | | 13.9 | 16.8 | | −2.8 | | | | | |
| ESM $10^{-14}$ M | | 17.6 | 20.3 | | | | | | ACTB | |
| SM1 | D(−13/−15) | 14.0 | 17.7 | −3.7 | (+2.8) | −0.9 | 1.9 | 60000 | 114000 | |
| ESM $10^{-13}$ M | | 16.4 | 15.4 | | 1.1 | | | | | |
| ESM $10^{-14}$ M | | 20.2 | 19.0 | | | | | | MYC | |
| SM1 | D(−13/−15) | 23.7 | 23.9 | −0.2 | (−1.1) | −1.3 | 2.5 | 600 | 1500 | 13000 |

Note:
D(−13/−15) contains ACTB $10^{-13}$ M/target gene $10^{-15}$ M that corresponds to ACTB 60000/target gene 600 molecules. ISM, internal standards mixture; ESM, external standards mixture; SM1, surgically removed malignant sample1; NT Cq, native template cycle threshold; IS Cq, internal standard cycle threshold.

Calculation of Gene Expression: To quantify the copy number for each gene NT in a cDNA sample, 1) the $[NT\ Cq-IS\ Cq]_{Sample}$ for the unknown sample and the average [NT Cq−IS Cq] of two concentrations of ESM ($[NT\ Cq-IS\ Cq]_{ESM}$) were calculated, 2) The corrected delta Cq was calculated as: $[NT\ Cq-IS\ Cq]_{Sample}-[NT\ Cq-IS\ Cq]_{ESM}$, 3) $2^{(-corrected\ delta\ Cq)}$ was multiplied times the known number of input IS copies in the reaction to obtain the gene NT copy number, and 4) each target gene NT value was normalized to the ACTB loading control gene NT value, and presented as target gene NT molecules/$10^6$ ACTB molecules (Table 3, Table 4).

Accuracy: The concentration of each stock (purified) IS was determined using densitometric quantification of the appropriately sized peak after electrophoretic separation on the Agilent Bioanalyzer 2100. Then the appropriate volume of each IS was combined to make an ISM. After preparing the ISM, limiting dilution PCR and Poisson analysis were used to determine the true concentration of each IS in the ISM. Specifically, the stock ISM solution was serially diluted to a concentration expected to contain 40, 20, 10, 7, 4, 2, 1, 0.7, 0.4, 0.1 molecules of each IS in each microliter. The expected frequency of reactions with detectable PCR product at each dilution was tested with real time PCR using the pre-amplification method to increase the signal to background ratio (See the above section: Pre-amplification (1st round PCR) and second-round PCR). As an example, when 1 μl of the dilution expected to contain 0.7 molecules per microliter solution was included in the PCR, the expected frequency of positive reactions was 50.3% by Poisson analysis. The nine replicate samples of each dilution for each gene (ACTB, MYC, E2F1, CDKN1A) were measured. For each dilution the observed frequency of positive values (true concentration value) was plotted versus the frequency expected if the concentration determined by Agilent Bioanalyzer 2100 was correct.

Linearity: For each gene, the linearity of the assay was assessed through serial 10-fold dilution of the external standard stock solution ($10^{-11}$M NT/$10^{-11}$M IS to $10^{-17}$M NT/$10^{-17}$M IS) or serial dilution keeping IS constant and diluting NT up to 1/80-fold relative to IS and vice versa. For each dilution series, correlation coefficient ($r^2$) and slope (linearity) were calculated.

Imprecision: For each gene, the imprecision was measured as the coefficient of variation (CV) of the copy number measured at each dilution used in the linearity test. The CV was calculated as the standard deviation divided by the mean derived from multiple replicate measurements (at least three). The average CV across all dilutions for each gene, and the average CV across all four genes were calculated.

Robustness and Interference Tests: The effect of intentionally perturbing PCR conditions was assessed. Conditions altered included PCR volume and concentration of primer, probe, or EDTA. Samples used for this analysis were cDNA reverse transcribed from non-FFPE treated benign lung tissue RNA (Life Technologies, Grand Island, N.Y.) or FFPE-processed, surgically-removed, malignant lung tissue sample 1 or 8 RNA (SM1, SM8).

EDTA Concentration Variation: The effect of variation in PCR EDTA concentration on MYC and ACTB measurement was assessed in triplicate 20 μl PCR assays containing non-FFPE, benign lung cDNA pre-amplified with ISM. EDTA concentrations tested were 0, 0.5, 1, 1.4, 1.8, 2.2, 2.6, 2.8, 3.0, 3.2, 3.4, 3.6 and 4.0 mM.

Effect of ESM on Quality-Control: The effect of variation in fluorescence intensity on reliability of measurement was tested by varying ratio of [labeled probe]/[unlabeled probe] keeping [total probe] in the PCR constant at 200 nM. PCR assays were conducted for MYC and ACTB measurement in non-FFPE, benign lung cDNA pre-amplified with ISM. The IS labeled probe concentration in the PCR was kept constant while NT labeled probe was diluted with unlabeled probe to 200, 150, 100, 80, 40, 20, 10, 5, 0 nM or vice versa. Unlabeled probe was obtained from Life Technologies, Grand Island, N.Y.

Inter-day experimental variation without or with ESM was tested in FFPE sample SM8 cDNA in seven PCR reactions on five different days. The automatically selected Cq values were used to measure MYC/$10^6$ ACTB.

TABLE 4

Effect of external standards mixture (ESM) on quality control.
Inter-day experimental variation without and with ESM.

| | | | ACTB | | | | MYC | | | | |
|---|---|---|---|---|---|---|---|---|---|---|---|
| Sample | Day | ISM | NT Cq | IS Cq | Raw ΔCq | Molecules/ Assay | NT Cq | IS Cq | Raw ΔCq | Molecules/ Assay | MYC/$10^6$ ACTB |
| Without ESM correction | | | | | | | | | | | |
| SM8 | #1 | D(−12/−14) | 11.7 | 13.0 | −1.3 | 1.5E+06 | 16.7 | 18.5 | −1.8 | 2.1Eu+04 | 1.4E+04 |
| | #2 | D(−12/−14) | 11.8 | 11.3 | 0.5 | 4.3E+05 | 19.7 | 16.4 | 3.3 | 6.0E+02 | 1.4E+03 |
| | | E(−12/−15) | 11.7 | 11.0 | 0.7 | 3.7E+05 | 18.7 | 19.0 | −0.2 | 7.1E+02 | 1.9E+03 |
| | #3 | D(−12/−14) | 11.6 | 10.8 | 0.8 | 3.4E+05 | 19.8 | 16.9 | 2.9 | 8.1E+02 | 2.4E+03 |
| | | E(−12/−15) | 12.2 | 11.2 | 1.0 | 3.0E+05 | 19.8 | 20.4 | −0.6 | 9.0E+02 | 3.0E+03 |
| | #4 | D(−12/−14) | 18.0 | 16.6 | 1.4 | 2.3E+05 | 26.2 | 24.3 | 1.9 | 1.6E+03 | 7.0E+03 |
| | #5 | D(−12/−14) | 12.1 | 13.6 | −1.5 | 1.7E+06 | 20.2 | 19.7 | 0.5 | 4.3E+03 | 2.5E+03 |
| CV | | | | | | 0.90 | | | | 1.75 | 0.99 |
| With ESM correction | | | | | | | | | | | |
| SM8 | #1 | D(−12/−14) | −1.3 | −2.0 | 0.7 | 3.8E+05 | −1.8 | −3.0 | 1.2 | 2.5E+03 | 6.6E+03 |
| | #2 | D(−12/−14) | 0.5 | 0.0 | 0.4 | 4.5E+05 | 3.3 | 2.3 | 1.1 | 2.9E+03 | 6.5E+03 |
| | | E(−12/−15) | 0.7 | 0.0 | 0.6 | 3.8E+05 | −0.2 | 2.3 | −2.5 | 3.4E+03 | 8.8E+03 |
| | #3 | D(−12/−14) | 0.8 | −0.6 | 1.4 | 2.3E+05 | 2.9 | 1.7 | 1.2 | 2.7E+03 | 1.2E+04 |
| | | E(−12/−15) | 1.0 | −0.6 | 1.6 | 2.0E+05 | −0.6 | 1.7 | −2.3 | 2.9E+03 | 1.5E+04 |
| | #4 | D(−12/−14) | 1.4 | 0.5 | 0.9 | 3.3E+05 | 1.9 | 0.9 | 1.1 | 2.9E+03 | 8.8E+03 |
| | #5 | D(−12/−14) | −1.5 | −2.1 | 0.6 | 3.9E+05 | 0.5 | −0.5 | 1.0 | 3.0E+03 | 7.7E+03 |
| CV | | | | | | 0.27 | | | | 0.09 | 0.32 |

Statistical Analysis: The transcript abundance value (target gene molecules/$10^6$ ACTB molecules) for each LCDT gene was measured in triplicate and variation was measured as the CV. The Student's t-test was used to determine a significant ($P<0.05$) difference in mean LCDT value of the malignant group compared to the benign group. Levene's test was used to assess the equality of variances in different samples for Student's t-test using R program (v 2.15.2). The receiver operator characteristic (ROC) plot was generated by GraphPad Prism 6.

Results

Analytical Validation of Primers, Probes, and Internal Standard Mixtures

Primer Efficiency and Specificity: Primer efficiency was determined by PCR analysis of serially diluted IS. For each gene, at the dilution predicted to contain a single molecule of IS based on Agilent 2100 concentration analysis, the fraction of measured replicates that had detectable PCR product was consistent with the frequency predicted by Poisson analysis (see Accuracy section below). The Poisson analysis results support the conclusion that the IS concentration was accurate and that the primers had efficiency necessary to generate a detectable signal from a single molecule after 40 cycles.

Probe Specificity: For the first E2F1 assay design, the NT probe had >10% non-specific binding, so it was re-designed to increase the number of changes in IS compared to NT from four to six base pairs. After the re-design of the E2F1 IS and its respective probe, non-homologous (non-specific) binding was <1% for both NT and IS probes for all genes, more than meeting our threshold acceptance criteria.

Figure 3:
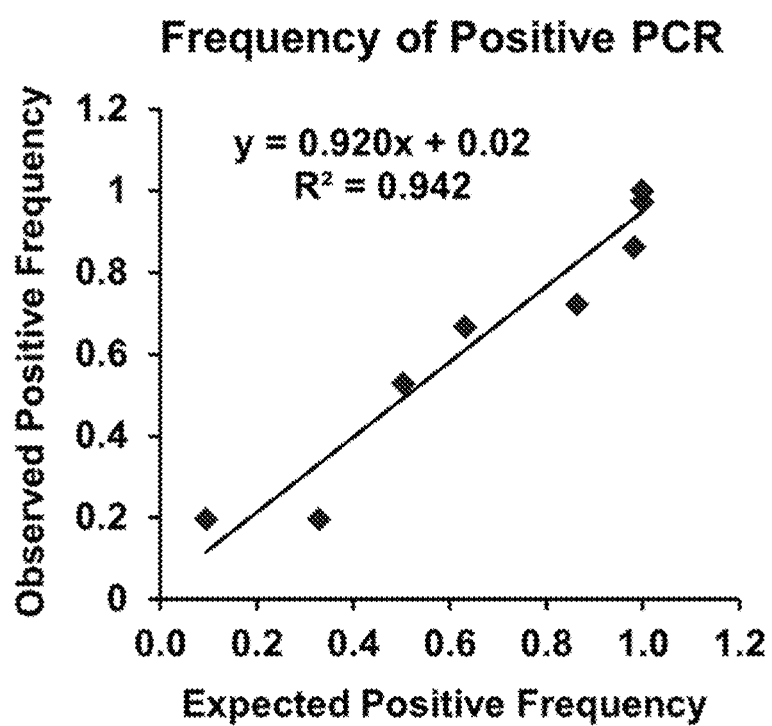
FIG. 3: Observed compared to expected positive PCR with limiting dilution. Frequency of observed relative to expected positive PCR signal was measured. Poisson analysis was used to calculate expected positive frequency. Results from the average of nine replicates at each of 10 internal standard mixture dilution points (40, 20, 10, 7, 4, 2, 1, 0.7, 0.4, 0.1 molecules/μl) averaged across the four genes (ACTB, MYC, E2F1, CDKN1A) were compiled and plotted. Each gene plot is presented in FIG. 4.
Figure 4A:
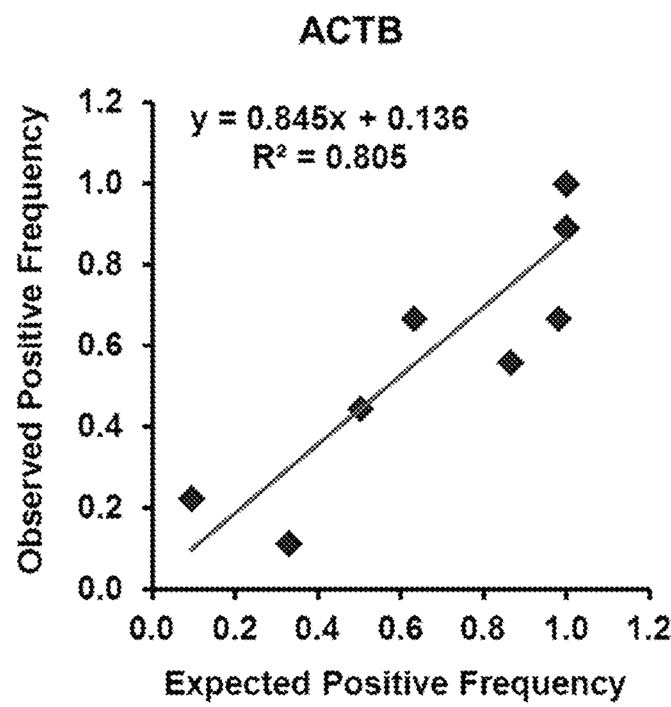
FIGS. 4A-4D: Frequency of positive PCR with limiting dilution PCR for each gene. Pre-amp method was used for testing 9 replicates of 10 dilution points (40, 20, 10, 7, 4, 2, 1, 0.7, 0.4, 0.1 molecules) for each gene.
Figure 4B:
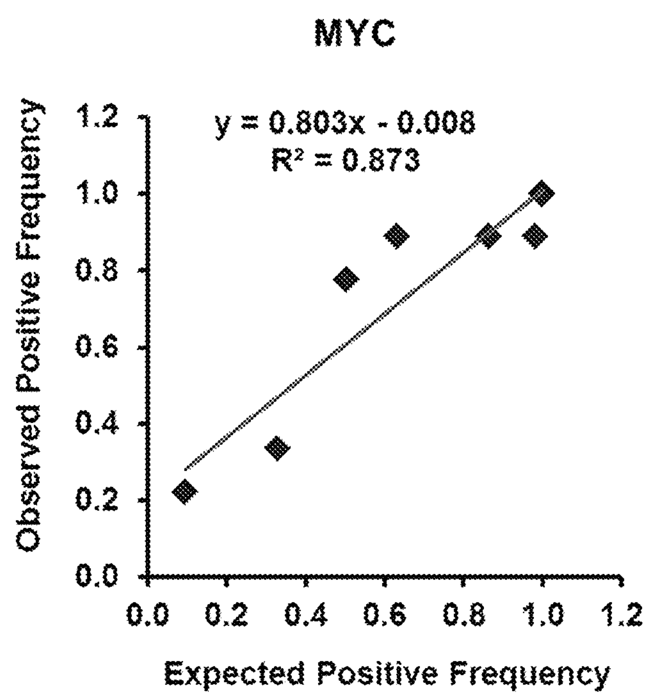
Figure 4C:
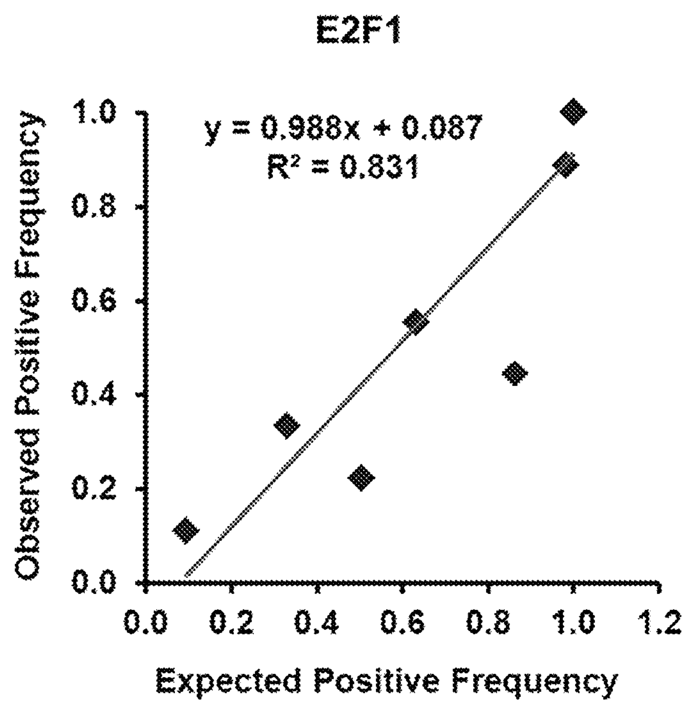
Figure 4D:
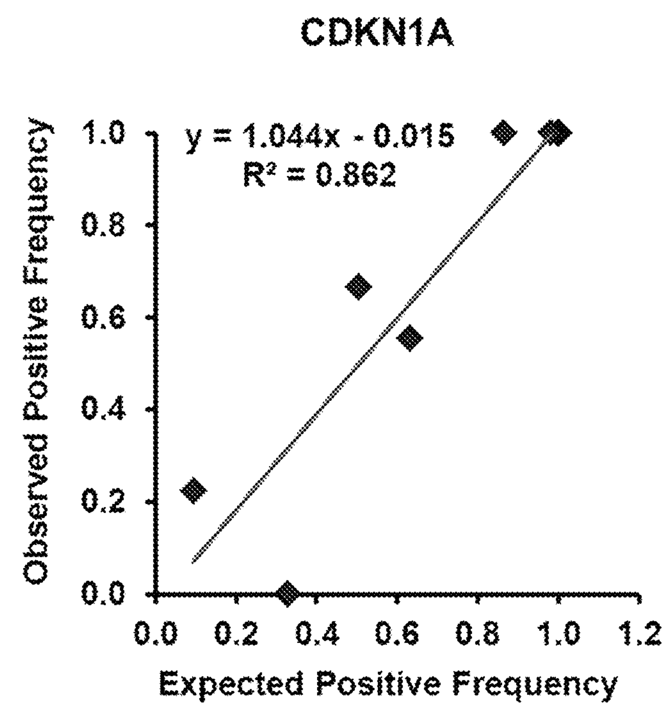

Internal Standards Mixture Accuracy: After the IS were combined into the ISM, the ISM was serially diluted beyond the level expected to contain a single molecule in a PCR assay, and the IS for each of the four genes was PCR-amplified in the PCR assays containing each ISM concentration. The observed frequency of the positive result was highly correlated ($R^2$=0.94) with the expected positive frequency predicted by Poisson analysis (FIG. 3, FIG. 4), indicating that the intended concentration for each IS in the ISM was accurate.

Analytical Validation of the Competitive Multiplex Two Color Real-Time Method

Figure 5A:
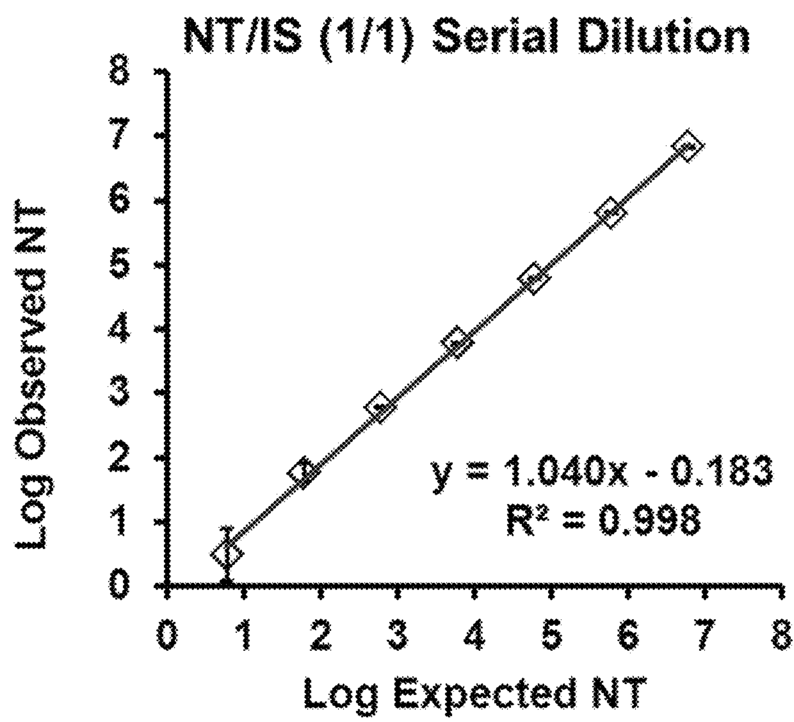
FIGS. 5A-5F: Linearity of the two-color fluorometric assay. Observed compared to expected E2F1 NT molecule values measured by two-color fluorometric assay in dilution series samples. Linearity graphs (FIGS. 5A, 5C, and 5E) and amplification plots of E2F1 (FIGS. 5B, 5D, and 5F).
Figure 5B:
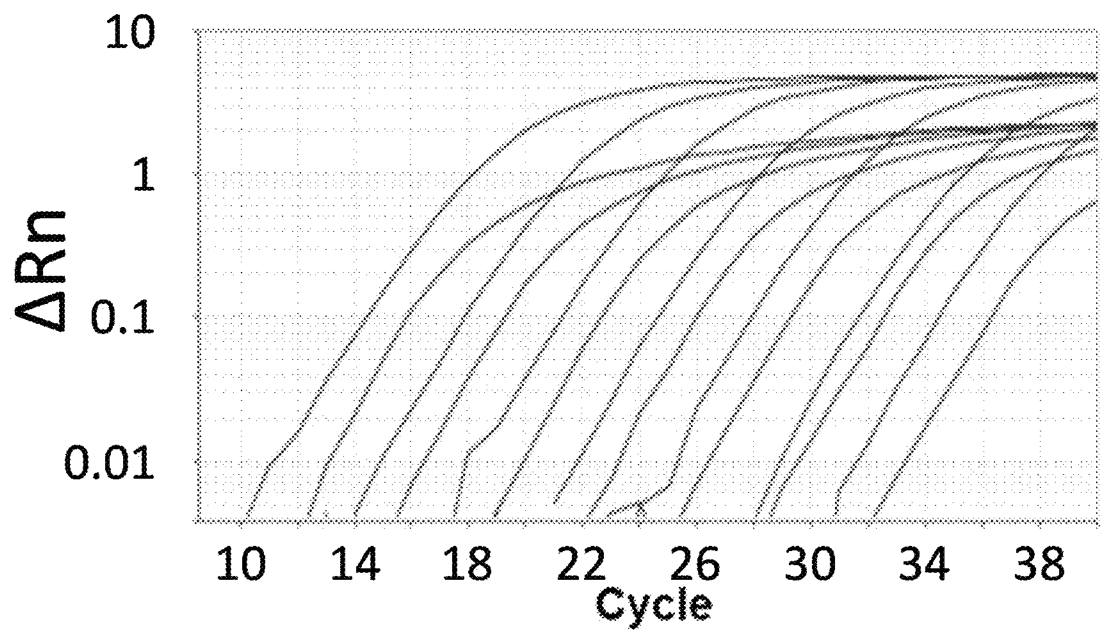
Figure 5C:
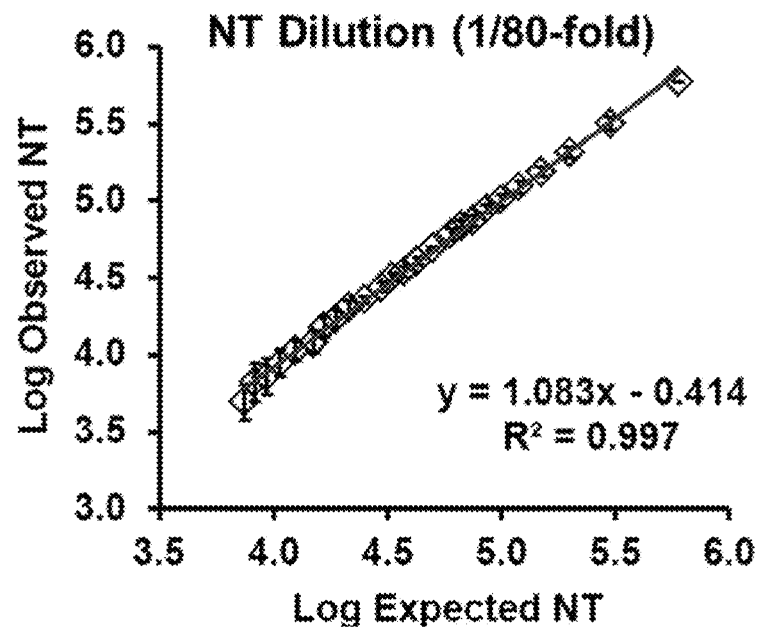
Figure 5D:
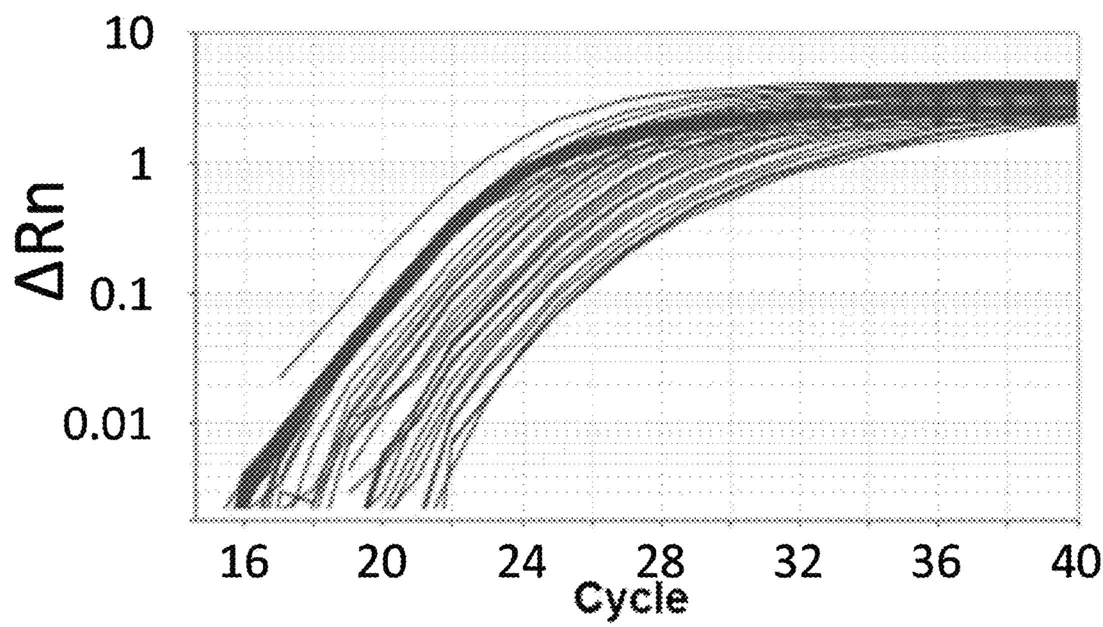
Figure 5E:
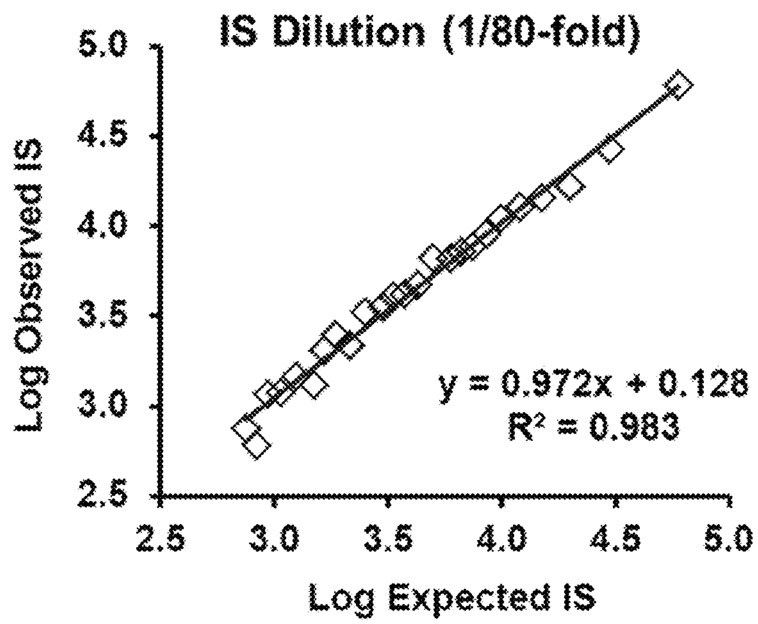
Figure 5F:
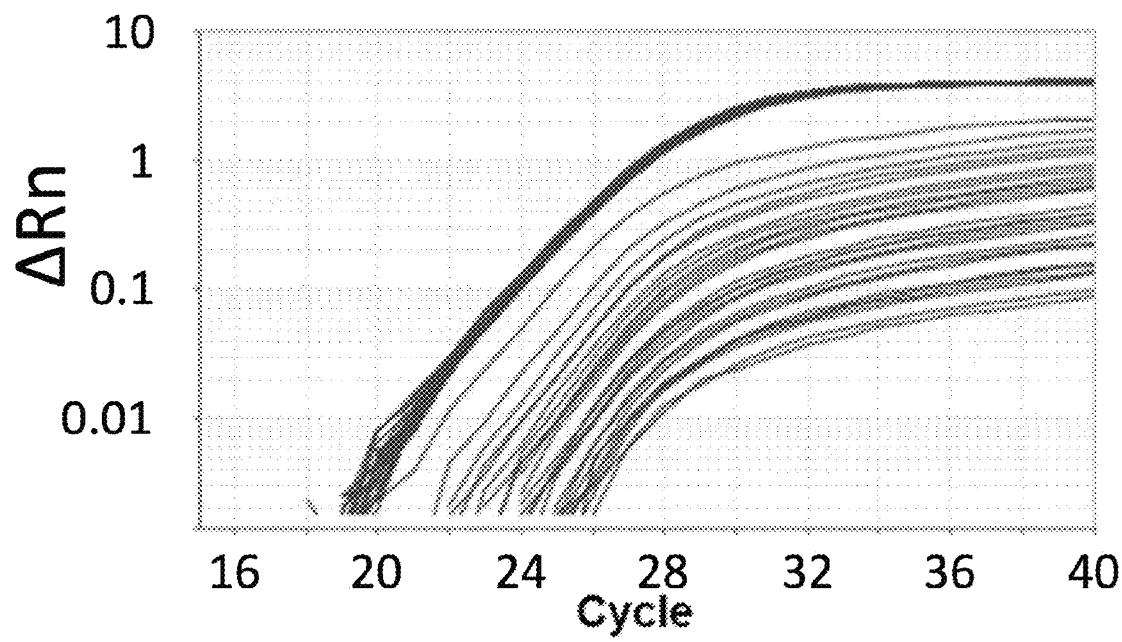
Figure 6A:
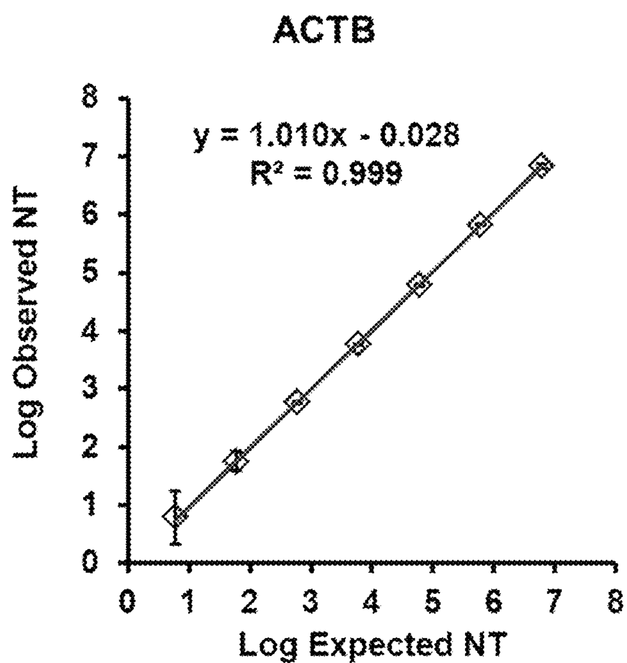
FIGS. 6A-6D: Linearity of the two-color fluorometric assay: Observed compared to expected native template (NT) molecule values measured by two-color fluorometric assay in external standards mixture (ESM) dilution series samples. ESM (1/1 mixture of NT and internal standard (IS)) was serial 10-fold diluted from NT $10^{-11}\underline{M}$/IS $10^{-11}\underline{M}$ to NT $10^{-17}\underline{M}$/IS $10^{-17}\underline{M}$ and each dilution sample analyzed in triplicate.
Figure 6B:
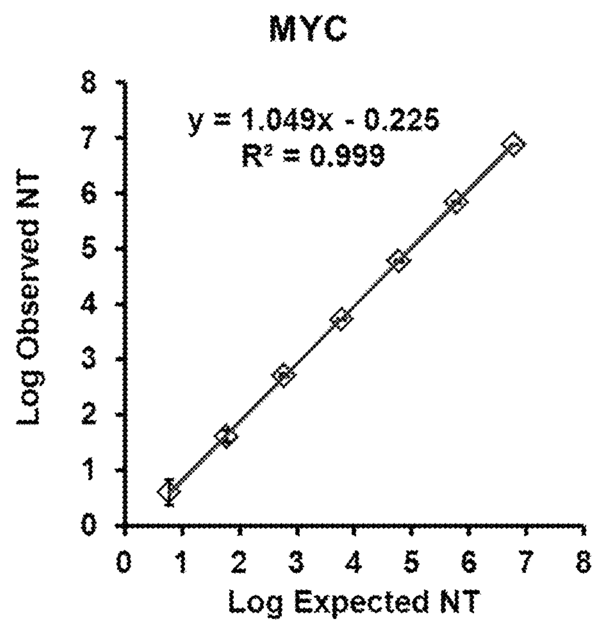
Figure 6C:
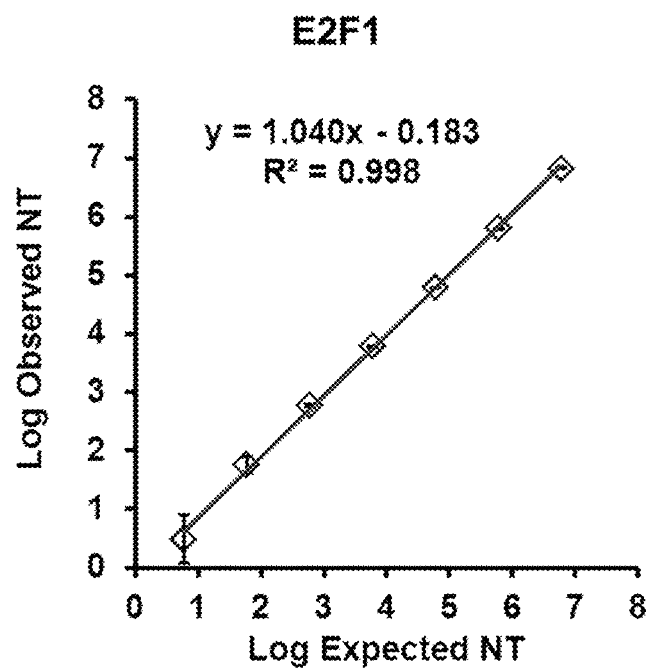
Figure 6D:
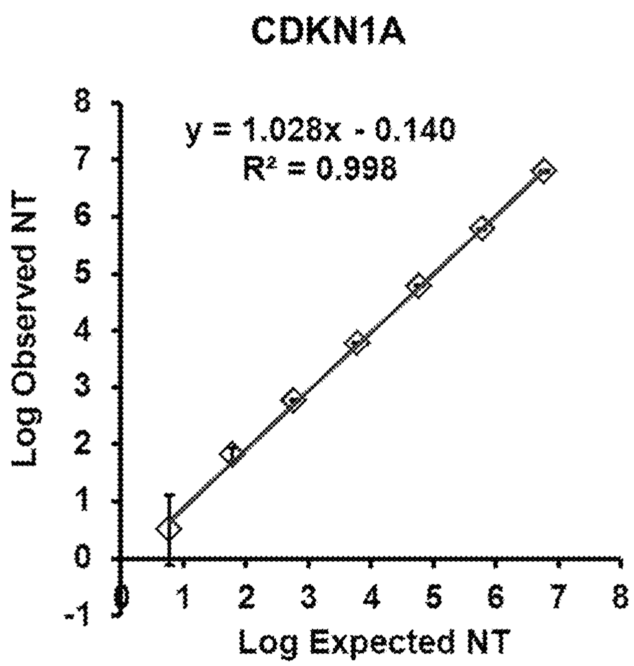
Figure 7A:
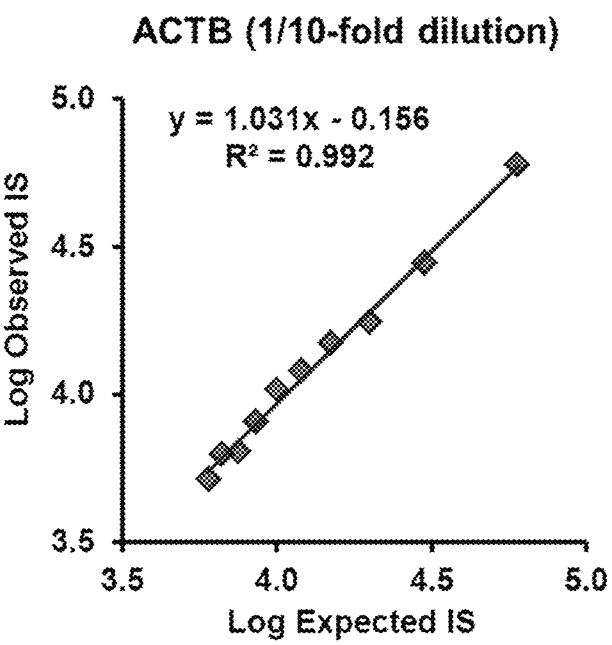
FIGS. 7A-7H: Linearity of the two-color fluorometric assay: Observed compared to expected NT molecule values measured by two-color fluorometric assay in serially diluted synthetic internal standard (IS) relative to constant synthetic native template (NT) dilution series samples. ACTB, MYC, E2F1, or CDKN1A synthetic IS was serially diluted relative to constant synthetic native template (NT) starting with 1/1 of NT/IS mixture at $10^{-13}$M.
Figure 7B:
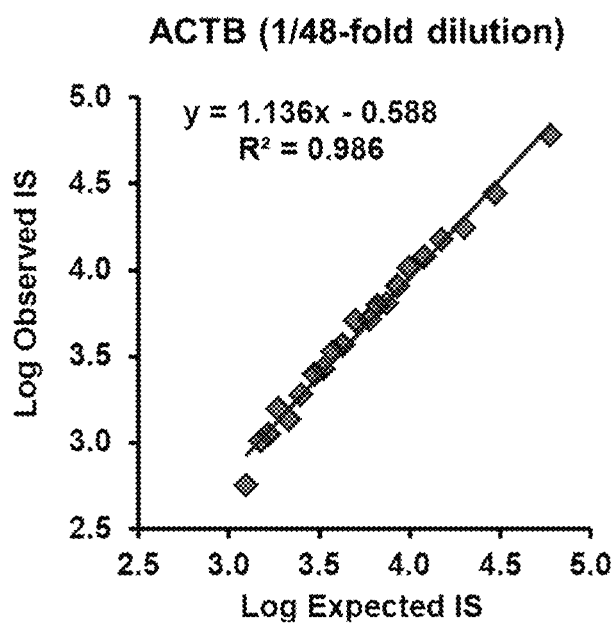
Figure 7C:
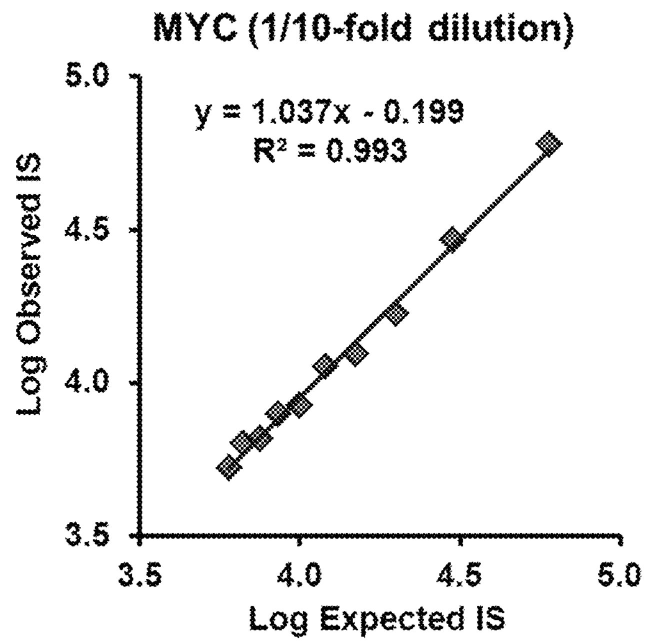
Figure 7D:
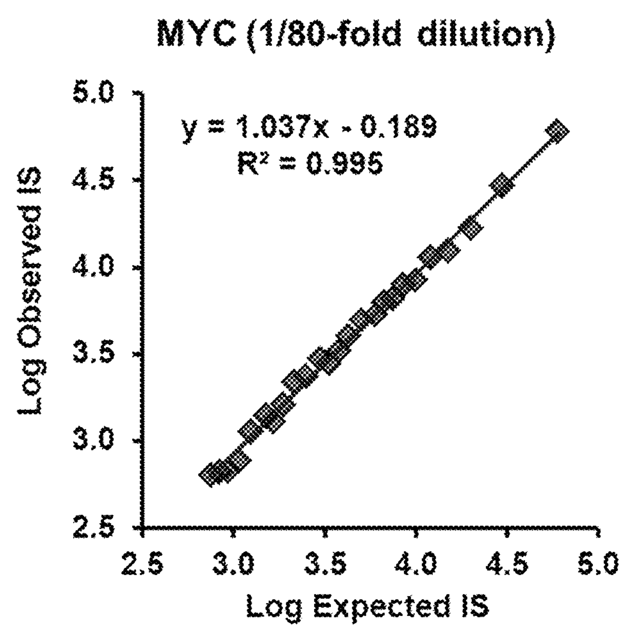
Figure 7E:
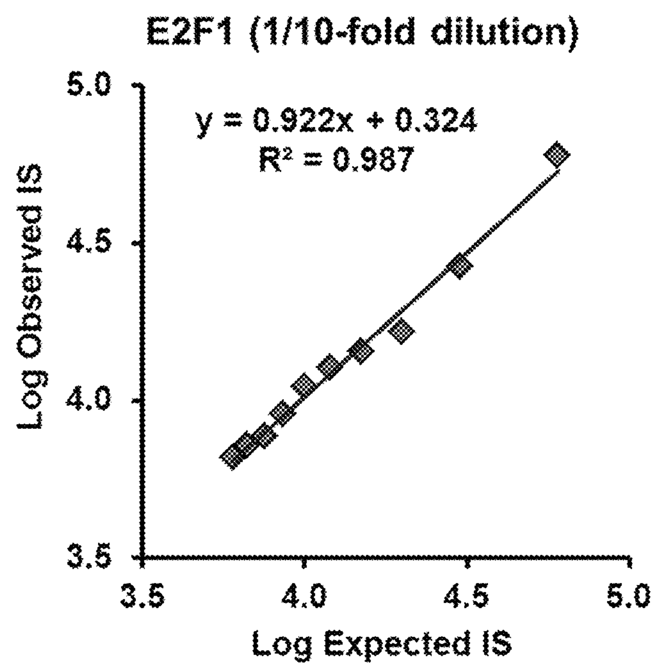
Figure 7F:
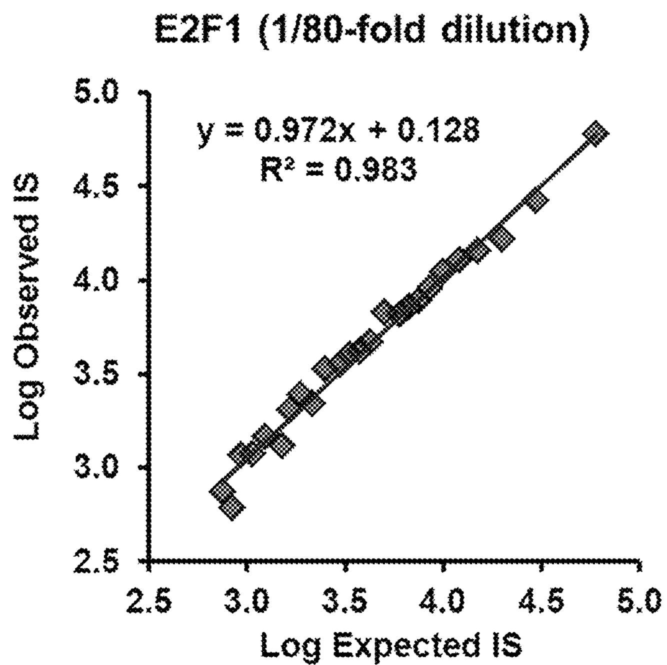
Figure 7G:
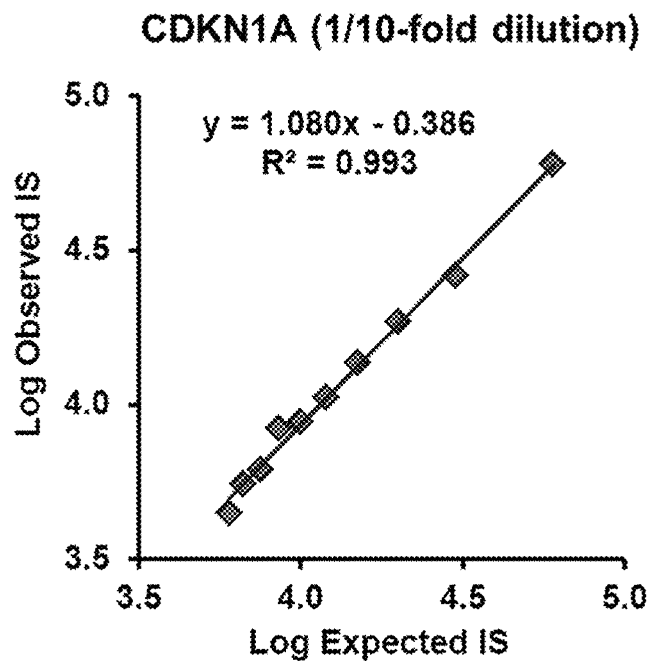
Figure 7H:
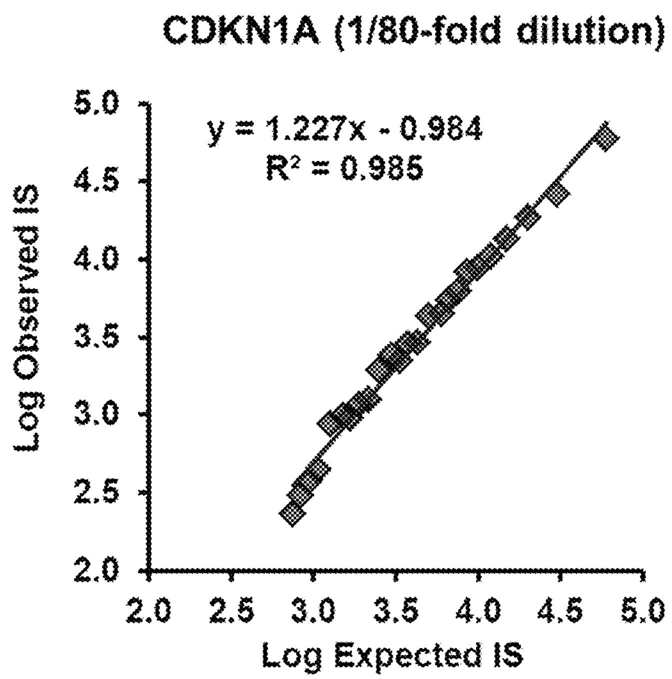

Linearity: The linearity of the two-color fluorometric assay was determined by analysis of serial dilutions of synthetic NT and IS for each gene. In a serial dilution of the stock ESM (a 1/1 mixture of synthetic NT/IS) over seven orders of magnitude (from $10^{-11}$ M through $10^{-}17$ M), the correlation coefficient for the measurement of each gene relative to its respective IS was >0.99, and the average slope for the signal-to-analyte response was 1.0±0.05 (FIGS. 5A-5B, FIG. 6).

To more stringently assess linearity, the NT was serially diluted relative to a constant IS concentration of $10^{-12}$M and the IS was diluted relative to a constant NT concentration of $10^{-13}$ M. In the dilutions with NT/IS or IS/NT ratio of ≤10, the average slope for the four genes (ACTB, E2F1, MYC, CDKN1A) was 1.0±0.10 in each set of dilution series. At dilutions with NT/IS or IS/NT≥10, there was a slight deviation of the slope from 1.0 (FIGS. 5C-5F, FIG. 7).

Imprecision: The imprecision for measurement of the LCDT genes was measured among both the ESM dilution samples and the NT/IS dilution samples. (FIGS. 5A-5F, FIG. 6, FIG. 7).

At each serial 10-fold dilution of ESM ($10^{-11}$M NT/$10^{-11}$ M IS to $10^{-17}$M NT/$10^{-17}$M IS), the average coefficient of variation (CV) for measurement of each of the four genes was <10% for >60 molecules input ($10^{-11}$ M NT/$10^{-11}$ M IS to $10^{-16}$M NT/$10^{-16}$M IS) and <30% for >6 molecules input ($10^{-11}$M NT/$10^{-11}$ M IS to $10^{-17}$M NT/$10^{-17}$M IS) with little inter-gene variation (Table 5).

Among the NT/IS dilution samples, the average CV among the four LCDT genes was calculated for different ranges of dilution. For an NT dilution from 1/1 to 1/10-fold relative to a constant IS, the average CV among the four genes was 12%. At dilutions beyond 1/10, the CV increased, but from 1/1 to 1/80 NT dilution the average CV was only 20% (Table 6). Similar results were observed for an average CV for each of the four genes in the IS dilution relative to a constant NT.

TABLE 5

Precision of the two-color fluorometric assay. A serially diluted 1:1 mixture of NT:IS from $10^{-11}$ M through $10^{-17}$ M was analyzed in triplicate.

| External standard | Expected NT | Average | SD | CV |
|---|---|---|---|---|
| (A) ACTB | | | | |
| $10^{-11}$ M | 6000000 | 6780000 | 600000 | 0.09 |
| $10^{-12}$ M | 600000 | 671000 | 16300 | 0.02 |
| $10^{-13}$ M | 60000 | 62600 | 2970 | 0.05 |
| $10^{-14}$ M | 6000 | 5880 | 207 | 0.04 |
| $10^{-15}$ M | 600 | 577 | 21 | 0.04 |
| $10^{-16}$ M | 60 | 61 | 26 | 0.42 |
| $10^{-17}$ M | 6 | 9 | 10 | 1.06 |
| Average of CV from $10^{-11}$ M to $10^{-16}$ M | | | | 0.11 |
| Average of CV from $10^{-11}$ M to $10^{-17}$ M | | | | 0.25 |
| (B) MYC | | | | |
| $10^{-11}$ M | 6000000 | 7590000 | 105000 | 0.01 |
| $10^{-12}$ M | 600000 | 700000 | 27500 | 0.04 |
| $10^{-13}$ M | 60000 | 61200 | 3190 | 0.05 |
| $10^{-14}$ M | 6000 | 5350 | 194 | 0.04 |
| $10^{-15}$ M | 600 | 515 | 39 | 0.08 |
| $10^{-16}$ M | 60 | 42 | 10 | 0.25 |
| $10^{-17}$ M | 6 | 4 | 2 | 0.43 |
| Average of CV from $10^{-11}$ M to $10^{-16}$ M | | | | 0.08 |
| Average of CV from $10^{-11}$ M to $10^{-17}$ M | | | | 0.13 |
| (C) E2F1 | | | | |
| $10^{-11}$ M | 6000000 | 6790000 | 221000 | 0.03 |
| $10^{-12}$ M | 600000 | 635000 | 13400 | 0.02 |
| $10^{-13}$ M | 60000 | 61400 | 1180 | 0.02 |
| $10^{-14}$ M | 6000 | 6100 | 114 | 0.02 |
| $10^{-15}$ M | 600 | 602 | 25 | 0.04 |
| $10^{-16}$ M | 60 | 60 | 20 | 0.34 |
| $10^{-17}$ M | 6 | 4 | 4 | 0.95 |
| Average of CV from $10^{-11}$ M to $10^{-16}$ M | | | | 0.08 |
| Average of CV from $10^{-11}$ M to $10^{-17}$ M | | | | 0.20 |
| (D) CDKN1A | | | | |
| $10^{-11}$ M | 6000000 | 6140000 | 260000 | 0.04 |
| $10^{-12}$ M | 600000 | 599000 | 10600 | 0.02 |
| $10^{-13}$ M | 60000 | 60800 | 1340 | 0.02 |
| $10^{-14}$ M | 6000 | 6000 | 138 | 0.02 |
| $10^{-15}$ M | 600 | 578 | 23 | 0.04 |
| $10^{-16}$ M | 60 | 68 | 20 | 0.29 |
| $10^{-17}$ M | 6 | 6 | 9 | 1.35 |
| Average of CV from $10^{-11}$ M to $10^{-16}$ M | | | | 0.07 |
| Average of CV from $10^{-11}$ M to $10^{-17}$ M | | | | 0.25 |

Figure 8A:
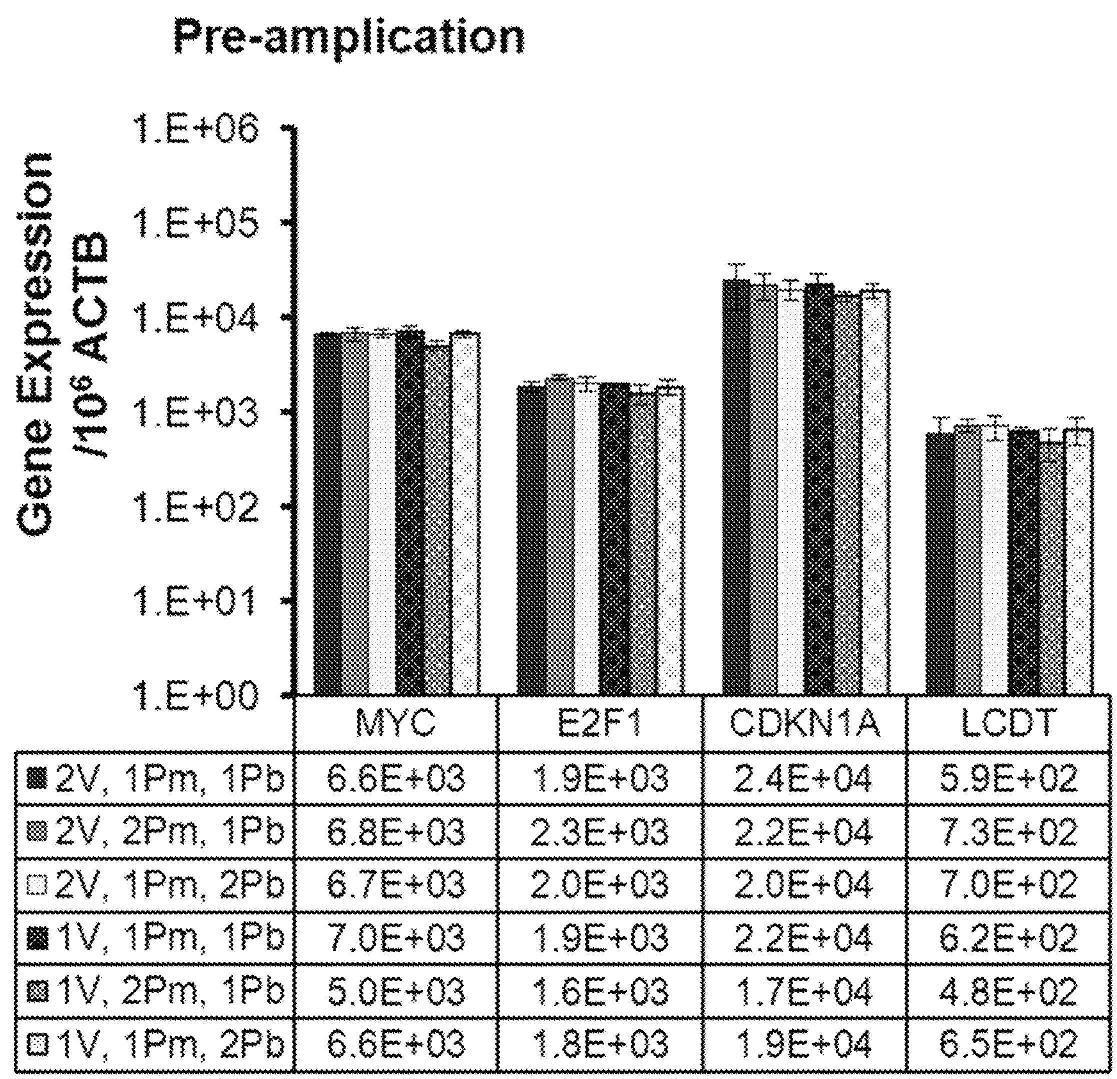
FIGS. 8A-8B: Effect of PCR reaction conditions on lung cancer diagnostic test (LCDT) gene expression values measured in cDNA with or without pre-amplification.
Figure 8B:
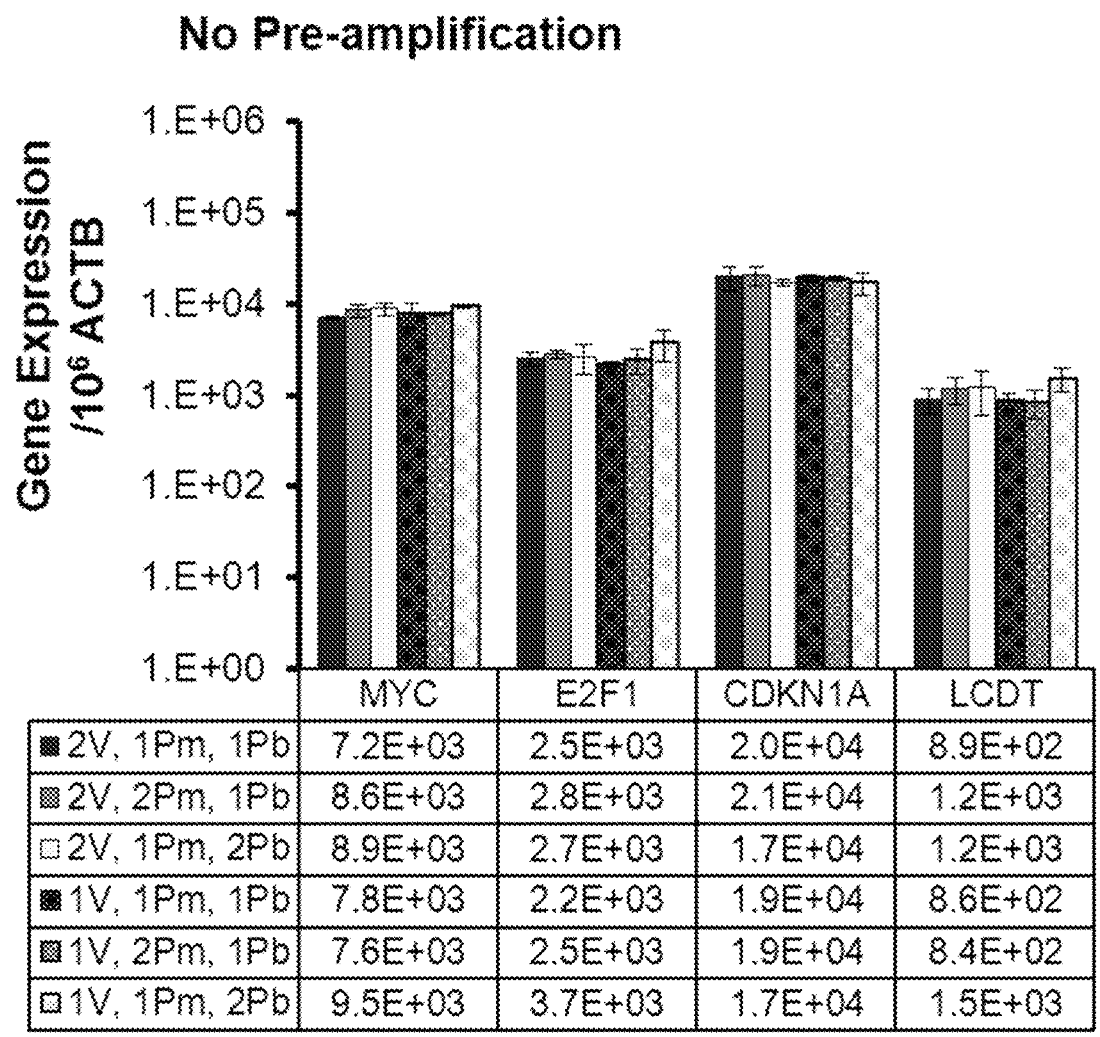
Figure 9:
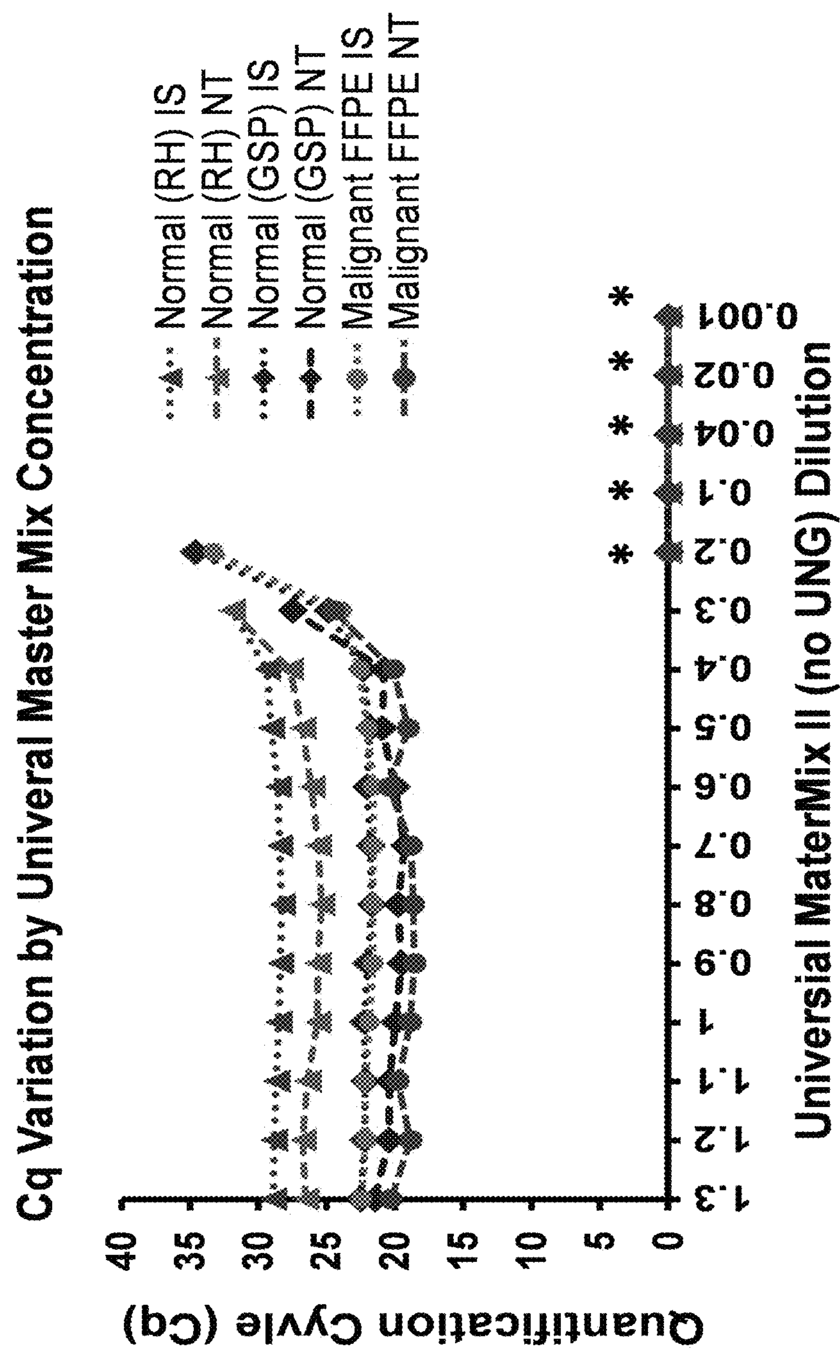
FIG. 9: Assay robustness by Universal Master Mix variance. Cq values of ACTB for surgically removed normal lung (RT with random hexamer (RH) and gene-specific primer (GSP)) and surgically removed formalin fixed paraffin embedded (FFPE) malignant (RT with GSP) are presented. Universal Master Mix II (no UNG) concentration was changed from 130% to 10% and ACTB was measured in three different kinds of cDNA. Note: the asterisk (*) indicates that Cq values were undetermined by software.

Robustness and Interference Testing: Changing the volumes and/or the concentrations of primers or probes did not lead to significant differences in expression measurement of MYC or ACTB in FFPE SM1 cDNA with or without pre-amplification (FIG. 8).

Figure 10A:
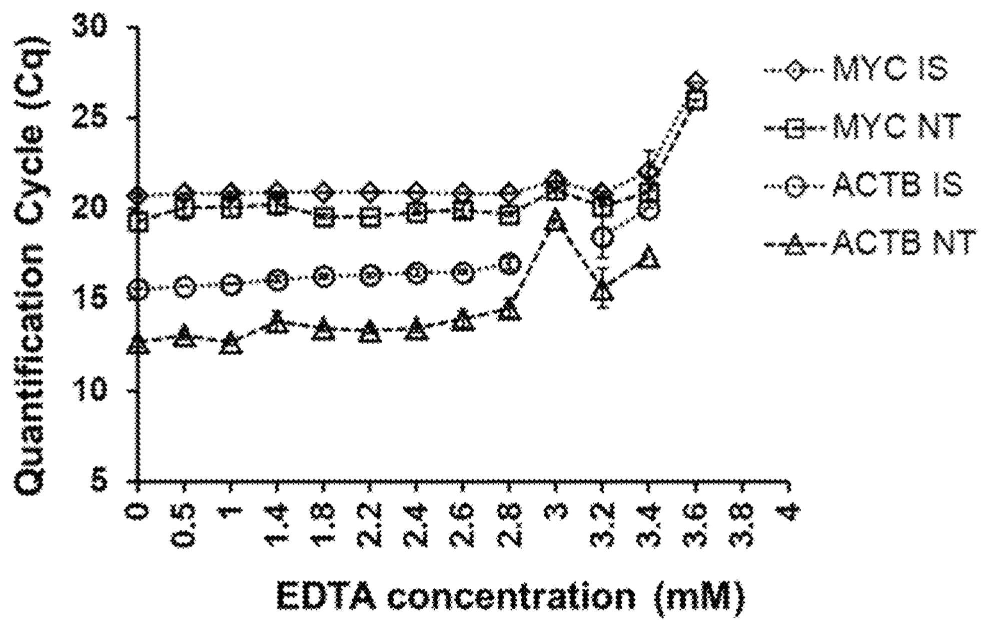
FIGS. 10A-10B: Internal standards control for PCR inhibition by EDTA. MYC and ACTB were measured in the presence of varying EDTA concentration.
Figure 10B:
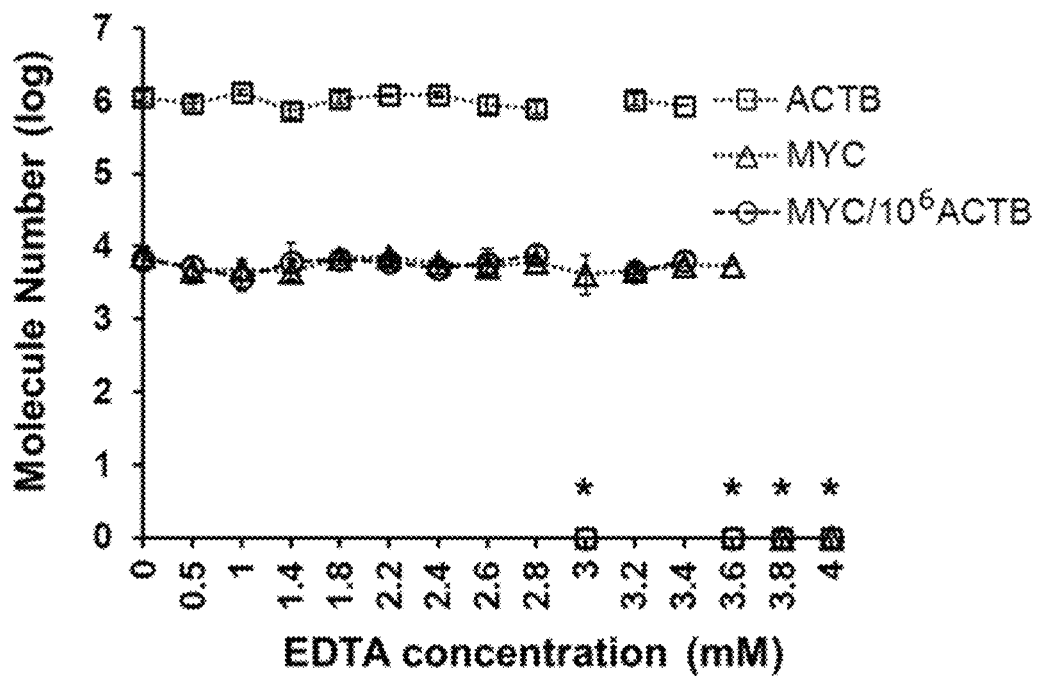

As EDTA concentration was increased, Cq value of each of the four analytes tested in non-FFPE, pre-amplified, benign lung cDNA (MYC IS and NT, ACTB IS and NT) increased, ultimately resulting in no signal (FIG. 10). However, the MYC NT and ACTB NT values calculated relative to their respective IS were constant, and due to the loss of signal for IS at highest EDTA concentration, no false negative values were reported.

Figure 11A:
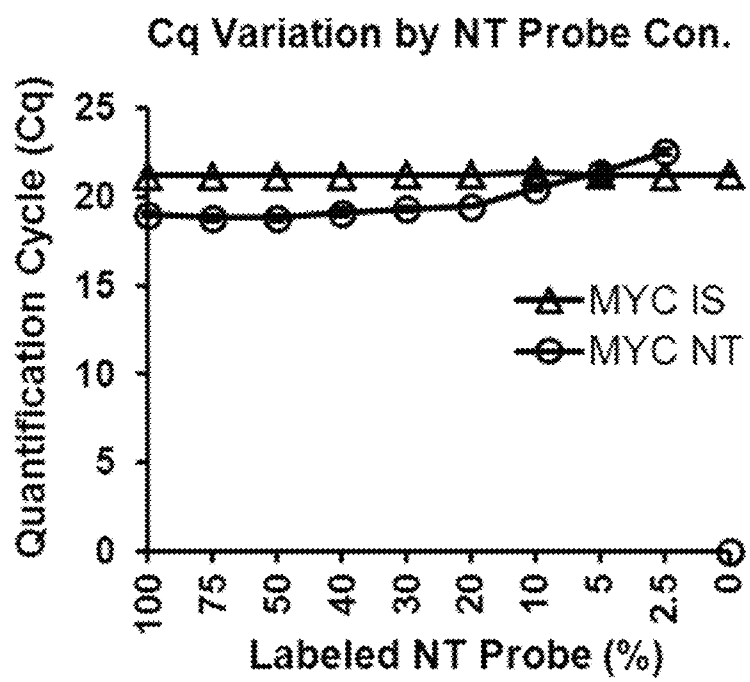
FIGS. 11A-11D: External standards mixture controls for inter-experimental variation in fluor signal or quantification cycle (Cq) selection.
Figure 11B:
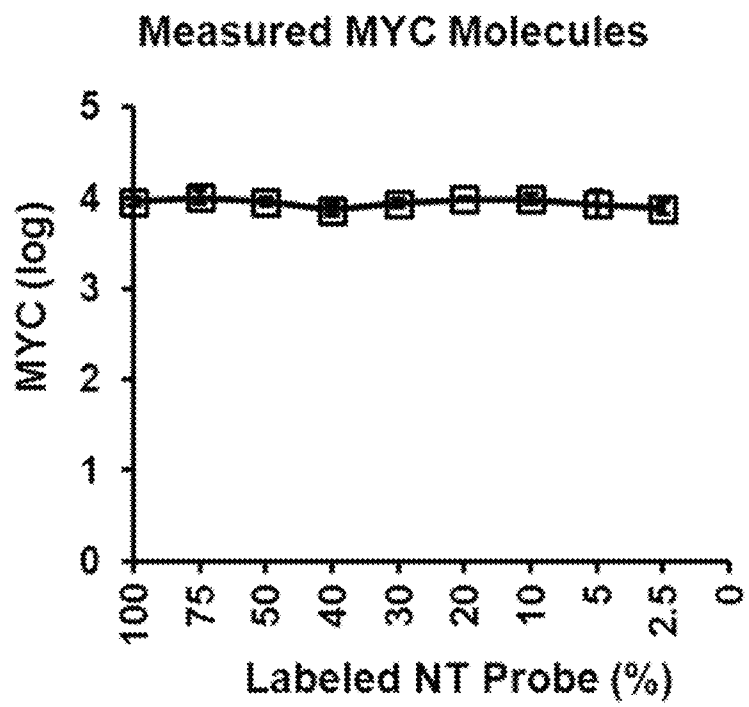
Figure 11C:
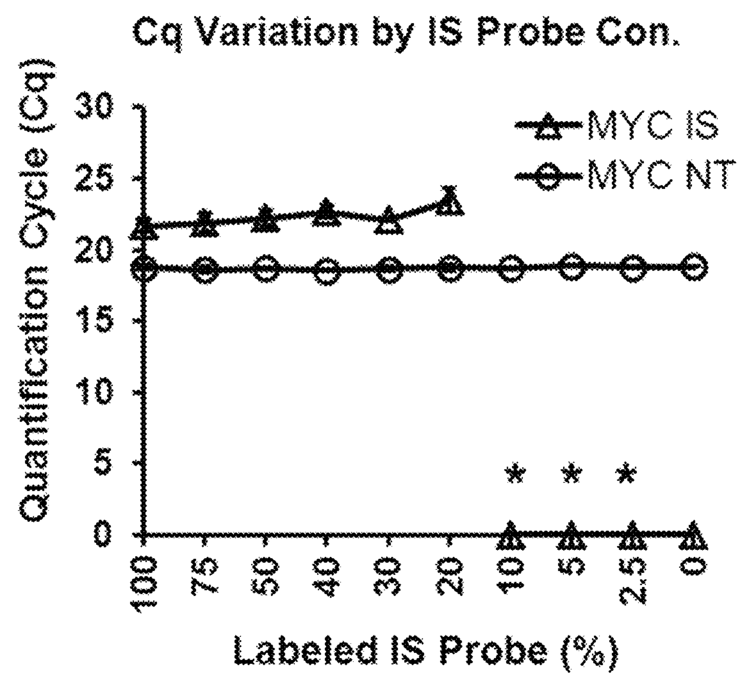
Figure 11D:
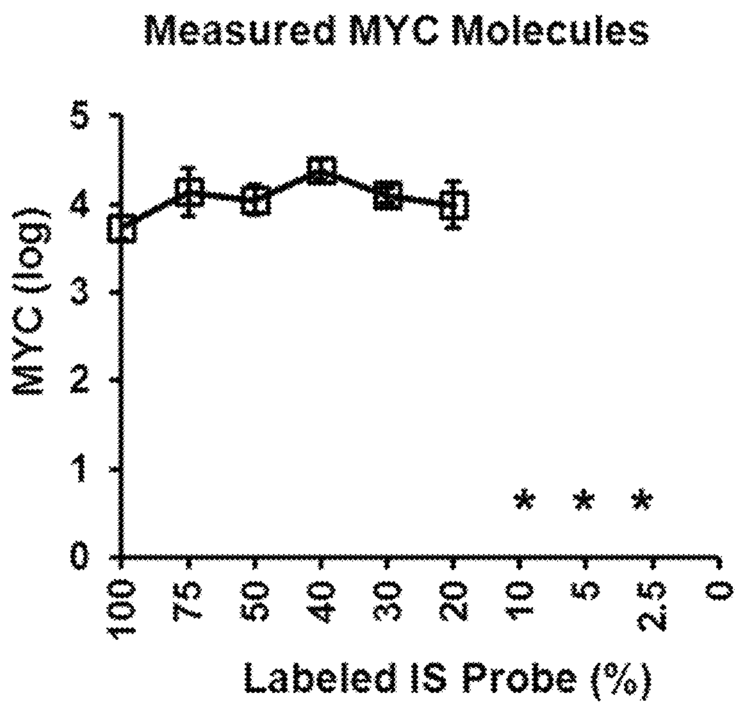

Use of ESM to Control for Variation in Fluorescent Labeling of Probe and Selection of Threshold The specific activity of probe labeling with fluor (i.e., [labeled probe]/[total probe]) may vary between experiments due to freezing and thawing of probes or due to lot differences, the effect of variation in fluorescence specific activity on measurement of MYC in benign, non-FFPE lung cDNA was tested. As the labeled probe concentration decreased in the reaction, the Cq increased (FIGS. 11A and 11C). However, this potential source of analytical variation was controlled by correcting the measured lung sample [NT Cq−IS Cq] values relative to the ESM [NT Cq−IS Cq] values (FIGS. 11B and 11D). The ESM contained a known 1:1 concentration of each NT and IS that was constant among experiments, therefore any variation in the observed ESM [NT Cq−IS Cq] relative to the expected value of 0 was attributable to variation in experimental conditions, including fluorescence intensity.

TABLE 6

Precision of the two-color fluorometric assay. For each gene serial dilution of keeping IS constant and diluting NT up to 1/80-fold relative to IS was measured in triplicate at each dilution. The compiled data of ACTB, MYC, E2F1 and CDKN1A are presented.

| NT Dilution | Expected NT | Average | SD | CV |
|---|---|---|---|---|
| NT 1/1 | 600000 | 600000 | 0 | 0 |
| NT 1/2 | 300000 | 317000 | 27600 | 0.09 |
| NT 1/3 | 200000 | 217000 | 33800 | 0.16 |
| NT 1/4 | 150000 | 156000 | 16800 | 0.11 |
| NT 1/5 | 120000 | 124000 | 11800 | 0.10 |
| NT 1/6 | 100000 | 99700 | 13400 | 0.13 |
| NT 1/7 | 85700 | 87400 | 13300 | 0.15 |
| NT 1/8 | 75000 | 71300 | 9900 | 0.14 |
| NT 1/9 | 66700 | 67400 | 9500 | 0.14 |
| NT 1/10 | 60000 | 61000 | 8800 | 0.14 |
| Average from 1/1 to 1/20 dilution | | | | 0.12 |
| NT 1/12 | 50000 | 48000 | 9200 | 0.19 |
| NT 1/14 | 42900 | 37300 | 6900 | 0.19 |
| NT 1/16 | 37500 | 31900 | 5000 | 0.16 |
| NT 1/18 | 33300 | 30600 | 4600 | 0.15 |
| NT 1/20 | 30000 | 27400 | 5200 | 0.19 |
| Average from 1/1 to 1/20 dilution | | | | 0.14 |
| NT 1/24 | 25000 | 22500 | 4600 | 0.20 |
| NT 1/28 | 21400 | 19100 | 4200 | 0.22 |
| NT 1/32 | 18800 | 16600 | 3900 | 0.23 |
| NT 1/36 | 16700 | 14600 | 4600 | 0.31 |
| NT 1/40 | 15000 | 12100 | 3700 | 0.31 |
| Average from 1/1 to 1/40 dilution | | | | 0.17 |
| NT 1/48 | 12500 | 10200 | 2500 | 0.25 |
| NT 1/56 | 10700 | 8000 | 2700 | 0.34 |
| NT 1/64 | 9380 | 6800 | 2300 | 0.34 |
| NT 1/72 | 8330 | 5700 | 2000 | 0.35 |
| NT 1/80 | 7500 | 3600 | 1600 | 0.45 |
| Average from 1/1 to 1/80 dilution | | | | 0.20 |

Another potential source of inter-experimental variation is inter-experimental variation in selection of Cq threshold. Even when the Auto Cq mode is used to select automatically the optimal Cq threshold, there was large inter-experimental variation in NT/IS Cq difference based on amplification plot and amount of cDNA loaded (FIG. 11E). Thus, whether the threshold was selected through the automatic method or the manual method, there was day-to-day variation in the selected Cq threshold setting. However, because the inter-experimental variation in the Cq threshold had the same effect on sample Cq and ESM Cq, inter-experimental variation in sample Cq was controlled by ESM Cq as described above. For example, MYC/$10^6$ ACTB was measured in FFPE sample SM8 cDNA in seven PCR replicates on five different days and the Cq threshold value automatically selected in each PCR was different (FIG. 11E) resulting in high CV of 0.99 (Table 4). However, with the ESM correction, the CV of measured MYC/$10^6$ ACTB was reduced to 0.32 (Table 4).

Fitness for Purpose Testing in FFPE Samples

Figure 14A:
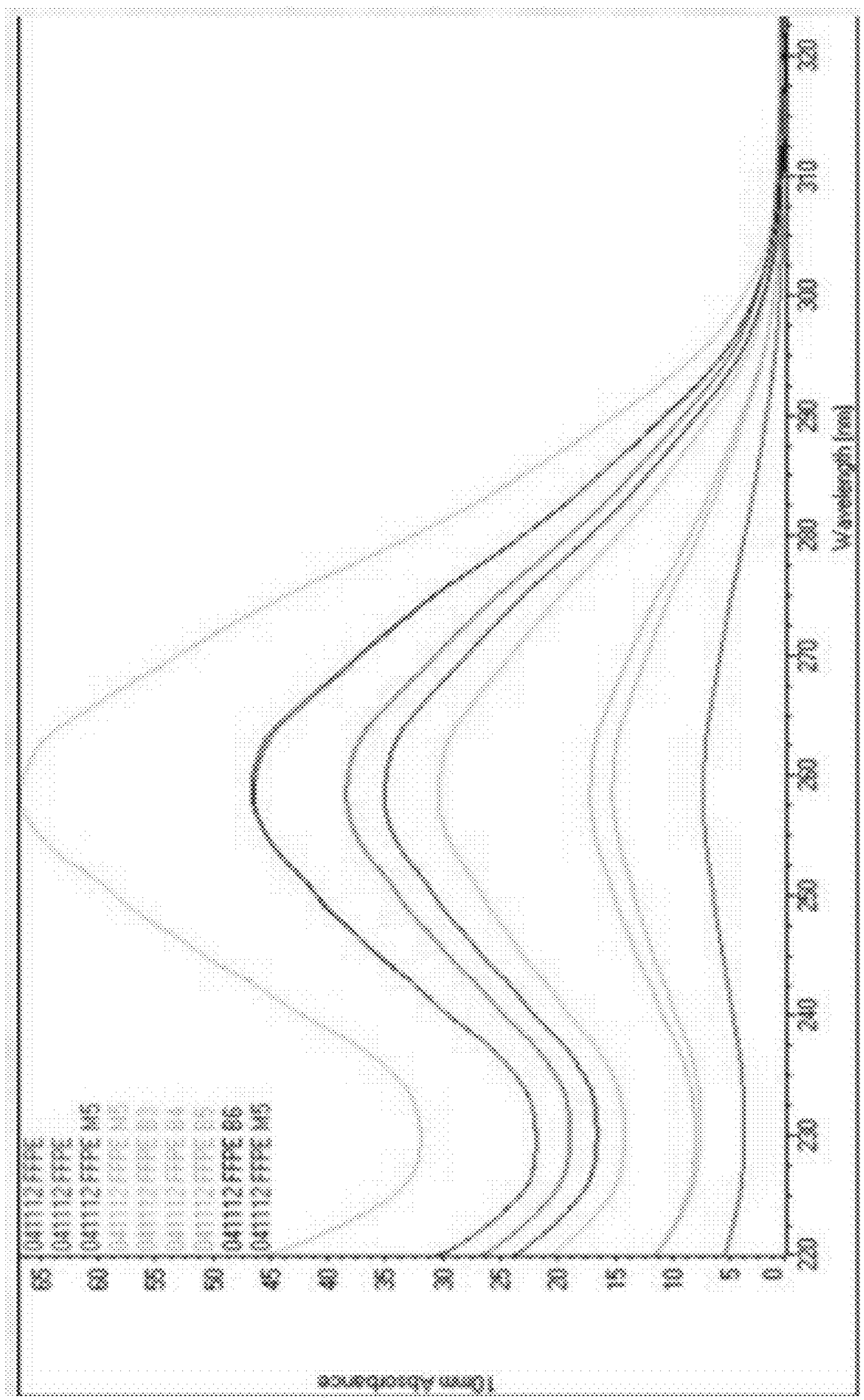
FIGS. 14A-14B: RNA extraction from surgically removed and fine needle aspirate formalin fixed paraffin embedded samples.
Figure 14B:
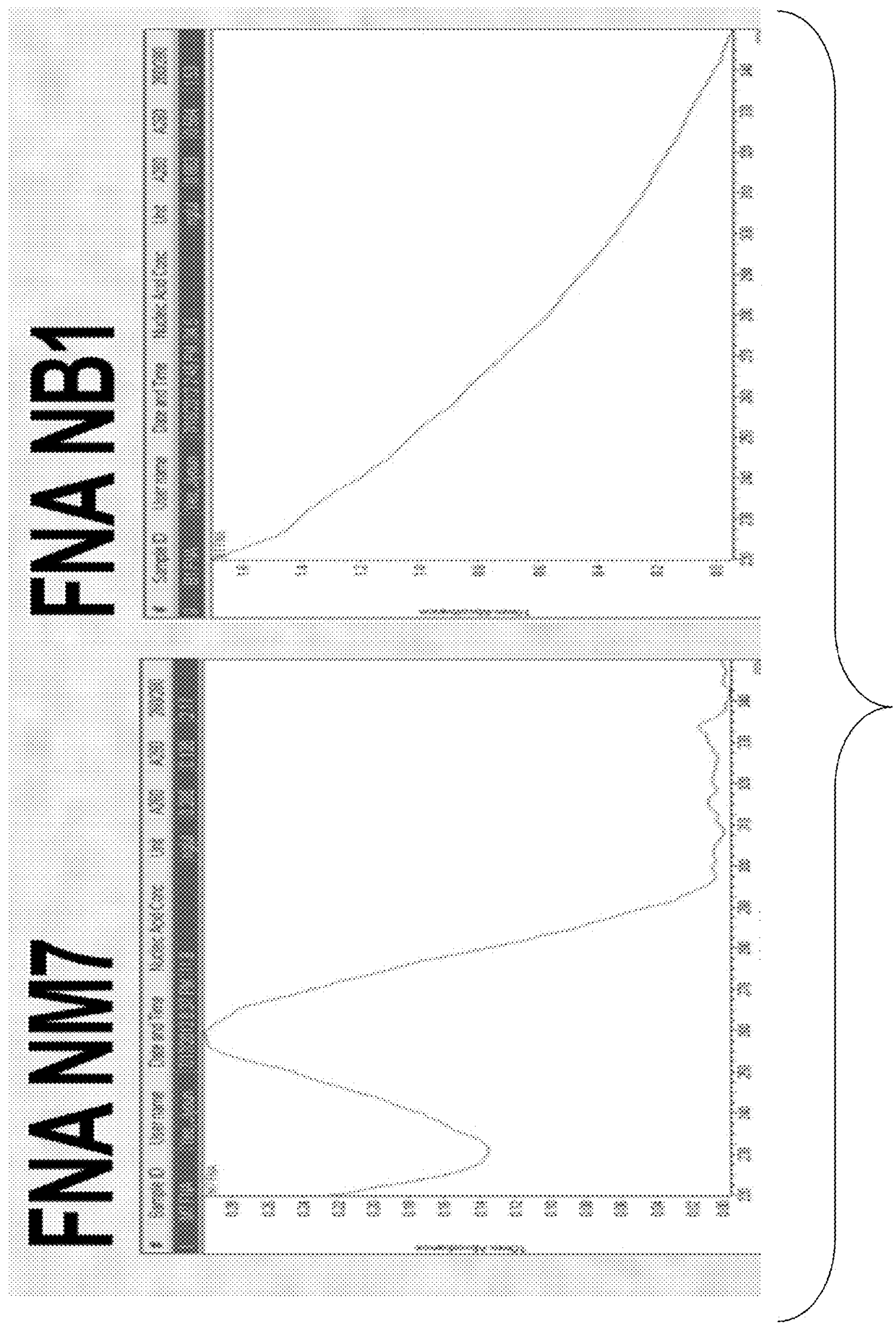
Figure 14:
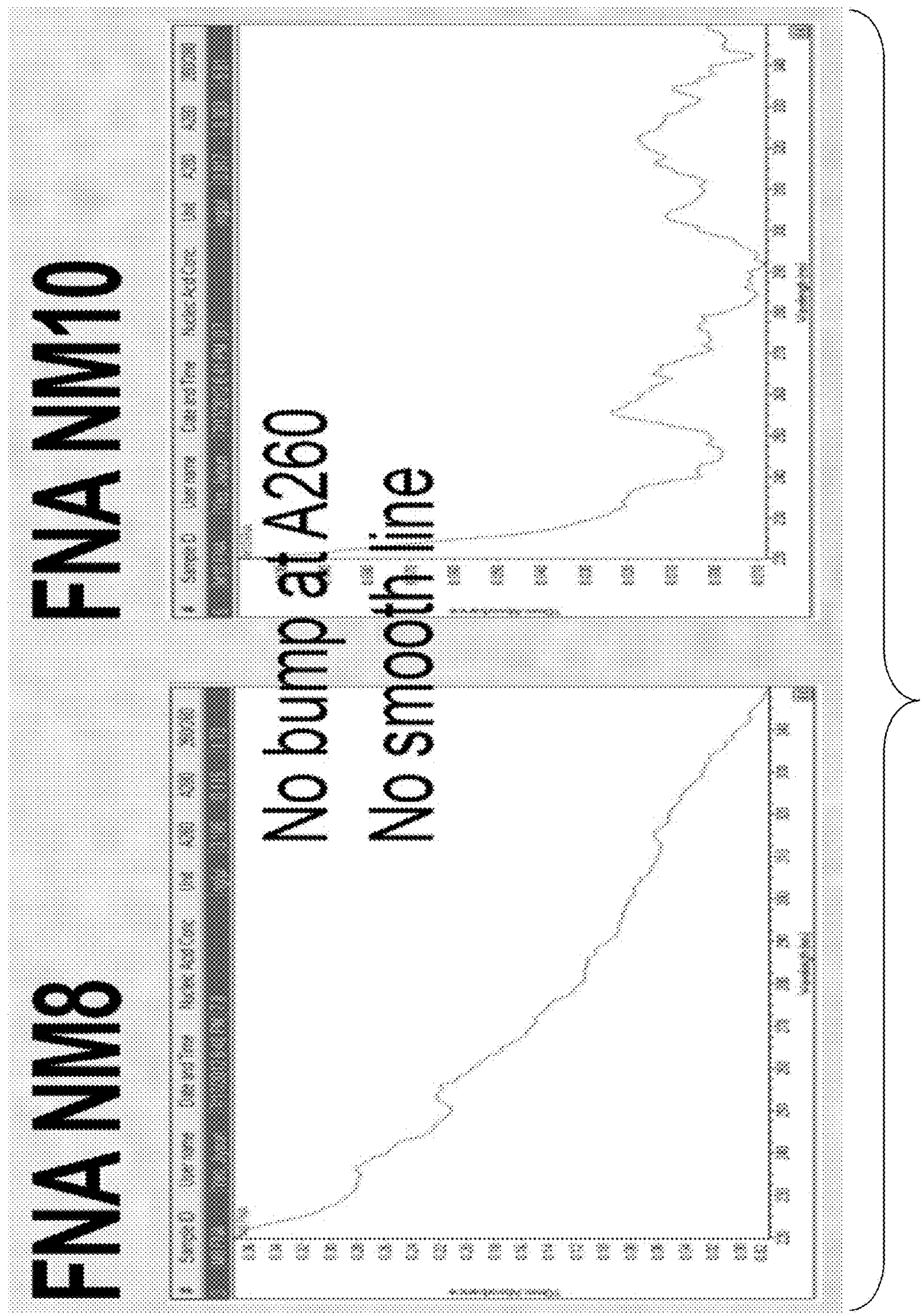

The histomorphologic diagnosis of benign or malignant FFPE samples used in this study is presented in Table 7. The RNA yield and purity are presented in Table 8 and FIG. 14.

TABLE 7

Biological characteristics of surgical FFPE sample subjects.

| | Benign | | Malignant |
|---|---|---|---|
| SB1 | TB | SM1 | Squamous cell carcinoma |
| SB2 | Emphysema | SM2 | Adenocarcinoma |
| SB3 | UIP | SM3 | Squamous cell carcinoma |
| SB4 | COPD | SM4 | Adenocarcinoma |
| SB5 | Emphysema | SM5 | Squamous cell carcinoma |
| SB6 | UIP | SM6 | Adenocarcinoma |
| SB7 | Foreign body granulomas | SM7 | Adenocarcinoma |
| SB8 | DAD | SM8 | Adenocarcinoma |
| SB9 | Granulomas | SM9 | Squamous cell carcinoma |
| SB10 | Pneumonia | SM10 | Adenocarcinoma |

TABLE 8

Comparison of FFPE RNA extraction kits. RNA extracted from FFPE-treated A549 cells was reverse transcribed in the presence of Reverse Transcription Standard Mixture (RTSM), that comprises known concentration of External RNA Control Consortium (ERCC) standards, non-endogenous alien sequences ERCC 171 (RNA) and ERCC 113 (cDNA).

| | RNeasy ® FFPE Kit (Qiagen) | | | | Absolutely RNA ® FFPE Kit (Agilent) | | | |
|---|---|---|---|---|---|---|---|---|
| Total thickness (μm) | 40 | 80 | 120 | 160 | 40 | 80 | 120 | 160 |
| Concentration (ng/μl) | 56 | 39 | 67 | 9 | 16 | 82 | 56 | 31 |
| Total RNA yield (ng) | 1680 | 1170 | 2010 | 260 | 480 | 2450 | 1690 | 940 |
| 260/280λ | 2.05 | 2.07 | 2.13 | 3.65 | 2.06 | 2.02 | 1.98 | 1.96 |
| RIN Score | 1.9 | 1.3 | 2.1 | 1 | 1 | 2.1 | 1.2 | 1 |
| RT efficiency (%) | 47.3 | 45.6 | 39.9 | 28.0 | 20.7 | 11.2 | 11.5 | 8.0 |

Figure 13:
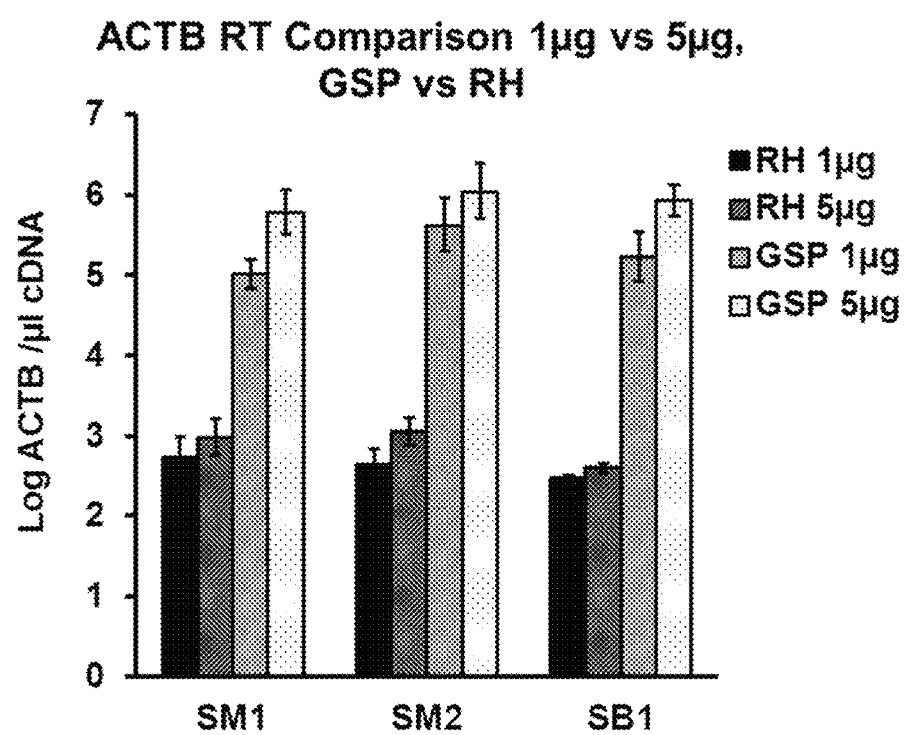
FIG. 13: Comparison of reverse transcription (RT) by priming method and RNA input. RT with gene-specific primer (GSP) showed a 660-fold ACTB cDNA increase compared to random hexamer (RH) with 1 μg of surgical formalin fixed paraffin embedded RNA samples, SM1, SM2, and SB1 in 30 μl RT reaction. When amount of RNA included in RT was increased to 5 μg from 1 μg, the yield of ACTB cDNA increased 4.6-fold in GSP-primed RT and 1.9-fold in RH-primed RT. SM1: malignant 1, SM2: malignant 2, SB1: benign 1.

Optimization of FFPE Reverse Transcription: Efficiency of RT with GSP or RHP was assessed in three (two malignant and one benign) surgical FFPE samples (SM1, SM2, SB1). The average yield of cDNA from 1 μg RNA was more than 50-fold higher with GSP. Based on this, analysis of FFPE samples was conducted with GSP in RT. The RT yield was increased another 4.6-fold by increasing RNA in RT to 5 μg (FIG. 13).

Effect of Pre-Amplification: Results for analysis of LCDT genes in sample SM1 with or without pre-amplification were compared to quantify the increase in signal relative to background resulting from pre-amplification and to confirm that it did not significantly alter the result. Importantly, for each gene the signal was increased (Cq decreased) with pre-amplification. Specifically, Cq value decreased for ACTB, MYC, E2F1, and CDKN1A by 9, 10, 9 and 10, respectively, following pre-amplification and 1000-fold dilution of the pre-amplification product prior to second round amplification. Yet, because each target was measured relative to a known number of its respective IS molecules, the value measured with the pre-amplification method was not significantly different from that measured with the no pre-amplification (FIG. 8).

Analysis of MYC, E2F1, CDKN1A and ACTB in FFPE Samples:

with a 95% confidence interval of 0.82 to 1.04 and the P-value of Student's t-test for stratification of malignant from non-malignant was 0.0061. The average CV among surgical FFPE samples for measurement of MYC, E2F1, and CDKN1A relative to ACTB was 0.27, 0.41, and 0.26, respectively (Table 9). These data confirm fitness for purpose of this optimized LCDT test in FFPE samples.

Discussion

The analytical validation and fitness for purpose testing of an RT-qPCR method suitable for reliable analysis of FFPE samples is described herein. Key features of this optimized method are highlighted here.

Internal Standards Provide Quality Control: The endogenous amount (NT) of each of multiple genes was measured relative to a known number of respective IS molecules. Each IS amplified with the same efficiency as the NT, and this controlled for inter-sample variation in PCR interfering substances and inter-experimental variation in PCR reagent quality or quantity or thermal cycling conditions as previously described. Key to the elimination of inter-experimental variation when measuring multiple genes was use of the same ISM comprising a known concentration of IS for each of the genes to be measured. The ISM was both stable and simple and inexpensive to prepare.

TABLE 9

Each gene measurement and lung cancer diagnostic test (LCDT) index in surgically removed, formalin-fixed, paraffin-embedded lung samples (n = 20).

| | MYC | | | E2F1 | | | CDKN1A | | | |
|---|---|---|---|---|---|---|---|---|---|---|
| | AVE | SD | CV | AVE | SD | CV | AVE | SD | CV | LCDT |
| Benign | | | | | | | | | | |
| SB1 | 1.5E+4 | 1.2E+4 | 0.83 | 6.7E+2 | 3.9E+2 | 0.58 | 3.6E+4 | 1.5E+4 | 0.41 | 2.8E+2 |
| SB2 | 2.1E+4 | 8.6E+3 | 0.42 | 1.3E+3 | 9.6E+2 | 0.77 | 5.8E+4 | 9.5E+3 | 0.16 | 4.5E+2 |
| SB3 | 4.1E+3 | 4.9E+2 | 0.12 | 2.8E+3 | 1.0E+3 | 0.35 | 3.1E+4 | 2.2E+3 | 0.07 | 3.8E+2 |
| SB4 | 7.4E+3 | 1.0E+3 | 0.14 | 1.5E+3 | 4.5E+2 | 0.30 | 3.0E+4 | 2.6E+3 | 0.09 | 3.6E+2 |
| SB5 | 1.8E+3 | 3.1E+2 | 0.17 | 1.4E+3 | 1.7E+2 | 0.12 | 1.1E+4 | 5.7E+2 | 0.05 | 2.4E+2 |
| SB6 | 3.2E+3 | 5.7E+2 | 0.18 | 1.3E+3 | 2.7E+2 | 0.20 | 4.1E+4 | 1.0E+4 | 0.25 | 1.1E+2 |
| SB7 | 8.1E+3 | 2.4E+3 | 0.30 | 7.5E+3 | 3.7E+3 | 0.49 | 4.0E+4 | 1.3E+4 | 0.32 | 1.5E+3 |
| SB8 | 9.5E+3 | 3.1E+3 | 0.33 | 1.3E+3 | 8.5E+2 | 0.65 | 5.4E+4 | 3.2E+3 | 0.06 | 2.3E+2 |
| SB9 | 6.6E+3 | 1.2E+3 | 0.18 | 7.1E+2 | 4.8E+2 | 0.69 | 2.4E+4 | 7.4E+3 | 0.31 | 2.0E+2 |
| SB10 | 2.7E+4 | 6.8E+3 | 0.26 | 9.5E+2 | 6.3E+2 | 0.66 | 7.6E+4 | 2.6E+4 | 0.35 | 3.3E+2 |
| AVE | | | 0.29 | | | 0.48 | | | 0.21 | |
| Malignant | | | | | | | | | | |
| SM1 | 1.5E+4 | 3.8E+3 | 0.25 | 6.1E+3 | 2.7E+3 | 0.45 | 5.1E+4 | 2.3E+4 | 0.45 | 1.8E+3 |
| SM2 | 7.4E+3 | 1.6E+3 | 0.22 | 8.2E+3 | 2.3E+3 | 0.28 | 2.2E+4 | 5.5E+3 | 0.25 | 2.8E+3 |
| SM3 | 1.2E+4 | 4.0E+3 | 0.33 | 1.2E+3 | 5.0E+2 | 0.43 | 1.6E+4 | 4.4E+3 | 0.28 | 8.9E+2 |
| SM4 | 1.4E+4 | 2.7E+3 | 0.20 | 1.2E+3 | 5.2E+2 | 0.43 | 4.4E+4 | 7.7E+3 | 0.17 | 3.8E+2 |
| SM5 | 1.2E+4 | 3.1E+3 | 0.26 | 1.8E+3 | 3.5E+2 | 0.20 | 1.8E+4 | 5.1E+3 | 0.29 | 1.2E+3 |
| SM6 | 7.7E+3 | 1.8E+3 | 0.23 | 4.2E+3 | 1.9E+3 | 0.45 | 1.9E+4 | 3.7E+3 | 0.20 | 1.7E+3 |
| SM7 | 9.3E+3 | 2.9E+3 | 0.31 | 2.0E+4 | 6.4E+3 | 0.31 | 5.0E+4 | 1.7E+4 | 0.33 | 3.8E+3 |
| SM8 | 9.8E+3 | 3.4E+3 | 0.35 | 2.8E+3 | 1.3E+3 | 0.47 | 3.6E+4 | 1.4E+4 | 0.39 | 7.6E+2 |
| SM9 | 1.3E+4 | 1.6E+3 | 0.12 | 3.2E+3 | 1.3E+2 | 0.04 | 2.6E+4 | 8.5E+3 | 0.33 | 1.7E+3 |
| SM10 | 1.0E+4 | 1.9E+3 | 0.19 | 2.4E+3 | 9.9E+2 | 0.41 | 2.9E+4 | 1.1E+4 | 0.40 | 8.7E+2 |
| AVE | | | 0.25 | | | 0.35 | | | 0.31 | |

Figures 12A, 12B:
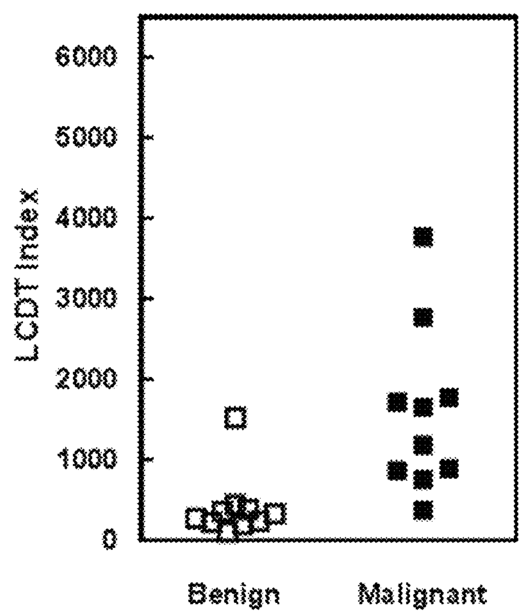
FIGS. 12A-12B: Validation of two-color fluorometric assay in 20 surgically removed, formalin fixed paraffin embedded lung samples.

The comparison of the LCDT index in benign and malignant surgical FFPE samples is presented in FIG. 12A, and the ROC curve analysis is presented in FIG. 12B. Based on the linearity and imprecision results, for analysis of clinical samples, the conditions for calculation of results were restricted tot/10 to 10/1-fold difference between the NT and the IS.

The LCDT optimal cut-off value had 90% specificity and 90% sensitivity to classify samples as cancer or non-cancer, similar to previous reports with non-FFPE fine needle aspirate (FNA) samples. The ROC area under the curve was 0.93

Two-Color Fluorometric Real-Time PCR: For reliable analysis of FFPE samples, it is important to use primers that yield short PCR products (e.g. 60-80 base pairs). Such products are readily quantified using real-time PCR. Competitive PCR analysis involves simultaneous quantification of each target gene NT and its respective IS. To do this by real-time PCR requires inclusion of two different sequence-specific probes in the same PCR reaction, each with a different fluor. Calculating each NT analyte relative to its respective IS requires an additional measurement, and, in some studies, this may be associated with a tendency to increase imprecision. However, the imprecision observed in the results described herein was less than 10% except for the measurement of very low copy numbers (<60 copies), at which point imprecision is determined largely by the natural law governing stochastic sampling variation rather than method-specific characteristics.

ESM Controlled for Inter-Run Variation in Probe Fluorescence: Multiple different factors may cause inter-experimental variation in fluor signal detection including variation in fluor concentration (FIGS. 11A-11D), variation in cycle threshold setting (FIG. 11E), and as yet unknown sources. The use of the ESM significantly reduced these sources of inter-experimental variation (Table 4). In addition to use in multiple analyte assays, such as the one presented here, this approach is applicable to single analyte two-color fluorometric assays and may demonstrate similar utility if so employed.

Multiplex Pre-Amplification Was Enabled by Use of Internal Standards: Using IS in conjunction with multiplex pre-amplification enabled reliable analysis of even lowly expressed genes in very small amounts of cDNA. Specifically, it was possible to determine the starting number of NT molecules, even after two rounds of PCR, by measuring the NT signal relative to the IS signal (FIG. 8). This is because a known number of its respective IS molecules was included in the pre-amplification reaction for each gene, and because the NT and IS amplified with the same efficiency.

Competitive multiplex pre-amplification improved measurement of FFPE samples in the following ways. First, cDNA consumption was reduced. In the multiplex pre-amplification, reduction in cDNA consumption depends on the number of targets and reference genes. Thus, in this study involving only three target genes and a single reference gene, cDNA consumption was reduced four-fold.

Second, pre-amplification markedly increased signal above the background signal typically observed in the no-template control at 35 Cq. Specifically, with one round of PCR (no pre-amplification) the Cq for each NT and IS ranged from 20-35. In contrast, using pre-amplified and 1000-fold diluted samples, the Cq for each NT and IS after a second round of PCR ranged from 11-26. The amount of dilution of first round amplification product can be reduced if necessary to ensure sufficient signal in the second round for very low input of sample cDNA. Further, for analysis of FNA FFPE samples with very low input cDNA, the higher signal following pre-amplification is associated with better precision than no pre-amplification.

Gene Specific Reverse Transcription: Use of gene specific priming in RT increases yield of cDNA by 10-100 fold compared to oligo dT or random hexamer priming when applied to RNA from human peripheral blood leukocytes. Because FFPE treatment typically reduces yield of cDNA from RNA by 100-fold, the utility of gene specific priming relative to random hexamer priming to increase signal was evaluated. The more than 50-fold increase in cDNA yield with gene specific priming RT compared to random hexamer priming RT observed in the results described herein study is consistent with previous studies with leukocytes.

Fitness of Method for FFPE Sample Analysis: Fitness of this two color fluorometric method for analysis of FFPE samples was evaluated by measuring a previously described test for lung cancer diagnosis for non-FFPE FNA samples in a small number of surgical FFPE benign and malignant lung samples. The results show the utility of this optimized method for analysis of FFPE samples. Specifically, imprecision was acceptable, and the optimal cut-off for the LCDT had similar accuracy in separating benign from malignant compared to what was reported previously for fresh FNA samples.

Diagnostic Applications

In some embodiments, a method of identifying a biological state is provided. In some embodiments, the method comprises measuring and/or enumerating an amount of each of 4 nucleic acids in a sample, providing the amounts as a numerical value; and using the numerical values to provide a numerical index, whereby the numerical index indicates the biological state.

A numerical index that indicates a biological state can be determined as described above in accordance with various embodiments. The sample may be obtained from a specimen, e.g., a specimen collected from a subject to be treated. The subject may be in a clinical setting, including, e.g., a hospital, office of a health care provider, clinic, and/or other health care and/or research facility. Amounts of nucleic acid(s) of interests in the sample can then be measured and/or enumerated.

In certain embodiments, where a given number of genes are to be evaluated, expression data for that given number of genes can be obtained simultaneously. By comparing the expression pattern of certain genes to those in a database, a chemotherapeutic agent that a tumor with that gene expression pattern would most likely respond to can be determined.

In some embodiments, methods described herein can be used to determine normal expression levels, e.g., providing numerical values corresponding to normal gene transcript expression levels. Such embodiments may be used to indicate a normal biological state, at least with respect to expression of the evaluated gene.

Normal expression levels can refer to the expression level of a transcript under conditions not normally associated with a disease, trauma, and/or other cellular insult. In some embodiments, normal expression levels may be provided as a number, or preferably as a range of numerical values corresponding to a range of normal expression of a particular gene, e.g., within +/− a percentage for experimental error. Comparison of a numerical value obtained for a given nucleic acid in a sample, e.g., a nucleic acid corresponding to a particular gene, can be compared to established-normal numerical values, e.g., by comparison to data in a database. As numerical values can indicate numbers of molecules of the nucleic acid in the sample, this comparison can indicate whether the gene is being expressed within normal levels or not.

In some embodiments, the method can be used for identifying a biological state comprising assessing an amount a nucleic acid in a first sample, and providing said amount as a numerical value wherein said numerical value is directly comparable between a number of other samples. In some embodiments, the numerical value is potentially directly comparable to an unlimited number of other samples. Samples may be evaluated at different times, e.g., on different days; in the same or different experiments in the same laboratory; and/or in different experiments in different laboratories.

In particular embodiments described herein, a method of identifying lung cancer is provided. In some embodiments, the method comprises measuring and/or enumerating an amount of each of 4 nucleic acids in a sample (ACTB, MYC, E2F1, and CDKN1A), providing the amounts as numerical values, and using the numerical values to provide a numerical index, whereby the numerical indicates the presence or absence of lung cancer.

Numerical indices that indicate the presence of lung cancer can be determined as described above in accordance with various embodiments.

Kits

The competitive internal standards (IS), external standards mixture (ESM), pairs of gene-specific primers (GSP), and fluorometric hydrolysis probes described herein may be assembled and provided in the form of kits. In some embodiments, the kit provides the IS, ESM, GSP, fluorometric hydrolysis probes, and reagents necessary to perform a PCR, including Multiplex-PCR and reverse transcription quantitative real-time PCR (RT-qPCR). The IS and ESM may be provided in single, concentrated forms where the concentrations are known, or serially diluted in solution to at least one of several known working concentrations.

The kits may include IS, ESM, and fluorometric hydrolysis probes specific to the three target genes (MYC, E2F1, and CDKN1A) and one reference gene (ACTB) of the lung cancer diagnostic test as described herein. The kits may include IS, ESM, and fluorometric hydrolysis probes specific to any gene or genes of interest.

The kits may also provide GSP designed specifically to amplify the IS and ESM of the lung cancer diagnostic test and their corresponding native targets, or any other gene or genes of interest. The kits may also provide one or more containers filled with one or more necessary PCR reagents, including but not limited to dNTPs, reaction buffer, Taq polymerase, and RNAse-free water. Optionally associated with such container(s) is a notice in the form prescribed by a governmental agency regulating the manufacture, use or sale of IS, ESM, and fluorometric probes and associated reagents, which notice reflects approval by the agency of manufacture, use or sale for research use.

The kits may include appropriate instructions for preparing, executing, and analyzing PCR, including Multiplex-PCR and RT-qPCR, using the IS, ESM, and fluorometric hydrolysis probes included in the kit. The instructions may be in any suitable format, including, but not limited to, printed matter, videotape, computer readable disk, or optical disc.

All publications, including patents and non-patent literature, referred to in this specification are expressly incorporated by reference herein. Citation of any of the documents recited herein is not intended as an admission that any of the foregoing is pertinent prior art. All statements as to the date or representation as to the contents of these documents is based on the information available to the applicant and does not constitute any admission as to the correctness of the dates or contents of these documents.

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof.

Therefore, it is intended that the invention not be limited to the particular embodiment disclosed herein contemplated for carrying out this invention, but that the invention will include all embodiments falling within the scope of the claims.

What is claimed is:

1. A kit for use in molecular diagnostic testing of lung cancer in a sample, comprising:

a) synthetic competitive internal standards (IS), individual IS comprising one each of: SEQ ID NO: 18; SEQ ID NO: 20; SEQ ID NO: 22; or SEQ ID NO: 24, wherein known quantities of each IS are formulated into an internal standards mixture (ISM);

b) an external standards mixture (ESM) comprising:

(1) purified synthetic native template (NT), individual NT comprising one each of: SEQ ID NO: 17; SEQ ID NO: 19; SEQ ID NO: 21; or SEQ ID NO:23; and (2) synthetic competitive internal standards (IS), individual IS comprising one each of: SEQ ID NO: 18; SEQ ID NO: 20; SEQ ID NO: 22; or SEQ ID NO: 24, wherein known quantities of each purified synthetic NT and IS are formulated into the ESM at a ratio in the range of 10:1 to 1:10;

c) pairs of gene-specific primers (GSP) specific to genes ACTB (forward primer: SEQ ID NO: 1; reverse primer: SEQ ID NO: 2), CDKN1A (forward primer: SEQ ID NO: 3; reverse primer: SEQ ID NO: 4), MYC (forward primer: SEQ ID NO: 5; reverse primer: SEQ ID NO: 6), and E2F1 (forward primer: SEQ ID NO: 7; reverse primer: SEQ ID NO: 8); and d) sequence-specific fluorometric hydrolysis probes, individual fluorometric hydrolysis probes comprising one each of: SEQ ID NO: 9; SEQ ID NO: 10; SEQ ID NO: 11; SEQ ID NO: 12; SEQ ID NO: 13; SEQ ID NO: 14; SEQ ID NO: 15; or SEQ ID NO: 16; wherein all fluorometric hydrolysis probes are labeled with a fluorescent reporter.

2. The kit according to claim 1, wherein SEQ ID NO: 9, SEQ ID NO: 11, SEQ ID NO: 13, and SEQ ID NO: 15 are labeled with FAM, and SEQ ID NO: 10, SEQ ID NO: 12, SEQ ID NO: 14, and SEQ ID NO: 16 are labeled with Quasar 670.

3. The kit according to claim 1, wherein the known quantities of each purified synthetic NT and IS are formulated into the ESM at a ratio of 1:1.

4. A method for using the kit according to claim 1 comprising the steps of:

a) extracting RNA from the sample;

b) reverse-transcribing (RT) the RNA extracted from the sample;

c) pre-amplifying cDNA generated by the RT of the RNA extracted from the sample along with the ISM, wherein the pre-amplification of the cDNA and ISM is done by polymerase chain reaction (PCR) using the pairs of GSP specific to the genes ACTB, CDKN1A, MYC, and E2F1;

d) performing a second round of PCR amplification of genes ACTB, CDKN1A, MYC, and E2F1, wherein a reaction mixture for a single gene comprises:

(1) a diluted pre-amplified cDNA and ISM product;

(2) a primer mixture comprising pairs of GSP corresponding to genes ACTB, CDKN1A, MYC, and/or E2F1;

(3) fluorometric hydrolysis probes specific for the single gene NT and corresponding IS;

e) along with the second round of PCR amplification simultaneously performing PCR amplification of each individual gene in reaction mixtures containing two distinct concentrations of the ESM, and primers and fluorometric probes for each individual gene NT and IS, wherein each distinct PCR reaction comprises the same fluorometric hydrolysis probes specific for the single gene NT and corresponding IS of step d)(3); and f) quantifying the copy number for loading control gene ACTB and target genes CDKN1A, MYC, and E2F1.

5. The method of claim 4, wherein, along with the second round of PCR amplification, the method further includes:

simultaneously performing PCR amplification of genes ACTB, CDKN1A, MYC, and E2F, wherein a reaction mixture for a single gene comprises:

(1) a first concentration of the ESM;

(2) the primer mixture comprising the pairs of GSP corresponding to genes ACTB, CDKN1A, MYC, and E2F1; and (3) fluorometric hydrolysis probes specific for the single gene NT and corresponding IS; and, repeating step e) using a second concentration of the ESM in place of the first concentration of the ESM, wherein the first concentration of the ESM and the second concentration of the ESM are distinct.

6. The method according to claim 4, wherein the two distinct concentrations of ESM differ by at least one order of magnitude.

7. The method according to claim 4, wherein the two distinct concentrations of ESM are $10^{-13}$ M NT/$10^{-13}$ M IS and $10^{-14}$ M NT/$10^{-14}$ M IS.

8. The method according to claim 4, wherein the step f) of quantifying the copy number for each target gene comprises the steps of:

a) calculating the difference in quantification cycle (Cq) between the NT and IS for a target gene using the formula $[\text{NT Cq}-\text{IS Cq}]_{Target\ Gene}$;

b) calculating an average difference in Cq between the NT and IS of two concentrations of ESM using the formula $([\text{NT Cq}-\text{IS Cq}]_{ESM\ Concentration\ 1}+[\text{NT Cq}-\text{IS Cq}]_{ESM\ Concentration\ 2})/2=[\text{NT Cq}-\text{IS Cq}]_{ESM}$;

c) calculating a corrected delta Cq using the formula $[\text{NT Cq}-\text{IS Cq}]_{Target\ Gene}-[\text{NT Cq}-\text{IS Cq}]_{ESM}$;

d) obtaining a target gene NT copy number by multiplying $2^{(-corrected\ delta\ Cq)}$ by a known number of input IS copies corresponding to the target gene in the reaction; and e) normalizing the target gene NT copy number to an ACTB gene loading control NT value.

9. The method of claim 4, wherein the samples comprise material having degraded RNA therein.

10. The method of claim 4, wherein the samples comprise formalin fixed paraffin embedded (FFPE) samples.

11. The method of claim 4, wherein the samples comprise fresh-frozen samples.

12. A kit for use in molecular diagnostic testing of a sample, comprising:

e) one or more synthetic competitive internal standards (IS), wherein each IS is synthesized to correspond with a unique target gene or reference gene, wherein an IS probe binding site has a 4-6 bp difference than that of a native template (NT), and wherein known quantities of the one or more IS are formulated into an internal standards mixture (ISM);

f) an external standards mixture (ESM) comprising:

(1) one or more purified synthetic NT, wherein each NT is synthesized to correspond with a unique target gene or reference gene; and (2) one or more synthetic competitive internal standards (IS), wherein each IS corresponds with a unique target gene or reference gene, wherein known quantities of each purified synthetic NT and IS are formulated into the ESM at a ratio in the range of 10:1 to 1:10;

g) one or more pairs of gene-specific primers (GSP), wherein each pair of GSP is specific for a unique target gene or reference gene, and is designed to amplify a PCR product having a product size of approximately 60-80 base pairs and span introns/exon splice junctions of the unique target gene or reference gene;

h) at least one pair of fluorometric hydrolysis probes, wherein each pair of fluorometric probes is specific for a unique target gene or reference gene, and comprises a first fluorometric hydrolysis probe that is sequence-specific for an NT probe binding site and is labeled with a first fluorescent reporter, and a second fluorometric hydrolysis probe that is sequence specific for an IS probe binding site of an IS corresponding to the NT against which the first fluorometric hydrolysis probe is sequence-specific for, and is labeled with a second fluorescent reporter.

13. The kit of claim 12, wherein in step b) 2), known quantities of each purified synthetic NT and IS are formulated into the ESM.

14. The kit of claim 13, wherein in step b) 2), known quantities of each purified synthetic NT and IS are formulated into the ESM at a ratio of 1:1.

15. The kit of claim 12, wherein in step b) 2), one or more synthetic competitive internal standards (IS) corresponds to each of the one or more purified synthetic NT.

16. The kit of claim 12, wherein the first fluorometric hydrolysis probe sequence-specific for the NT probe binding site is labeled with FAM, and the second fluorometric hydrolysis probe sequence specific for the IS probe binding site is labeled with Quasar 670.

17. A method for using the kit according to claim 16, comprising the steps of:

a) extracting RNA from the sample;

b) reverse-transcribing (RT) the RNA extracted from the sample;

c) pre-amplifying cDNA generated by the RT of the RNA extracted from the sample along with ISM including IS for each target gene or reference gene, wherein the pre-amplification of the cDNA and ISM is done by polymerase chain reaction (PCR) using the pairs of GSP specific to each target gene or reference gene;

d) performing a second round of PCR amplification for each target gene and at least one reference gene, wherein a reaction mixture for a single target gene or reference gene comprises:

(1) a dilution of the pre-amplified cDNA and ISM;

(2) a primer mixture comprising the one or more pairs of GSP;

(3) one pair of fluorometric hydrolysis probes, specific for a single target gene or reference gene and its corresponding IS;

e) along with the second round of PCR amplification, for each target gene or reference gene, simultaneously performing a PCR amplification on two distinct concentrations of the ESM containing the same pair of fluorometric hydrolysis probes used in step d)(3); and f) quantifying the copy number for each target gene.

18. The method of claim 17, wherein step e) further comprises simultaneously performing PCR amplification of target genes or reference genes, wherein a reaction mixture for a single gene comprises:

(1) a first concentration of the ESM;

(2) the primer mixture comprising the one or more pairs of GSP; and (3) fluorometric hydrolysis probes specific for the single target gene or reference gene NT and corresponding IS; and repeating step e) using a second concentration of the ESM in place of the first concentration of the ESM, wherein the first concentration of the ESM and the second concentration of the ESM are distinct.

19. The method according to claim 17, wherein the two distinct concentrations of ESM differ by at least one order of magnitude.

20. The method according to claim 17, wherein the two distinct concentrations of ESM are $10^{-13}$ M NT/$10^{-13}$ M IS and $10^{-14}$ M NT/$10^{-14}$ M IS.

21. The method according to claim 17, wherein the step of quantifying the copy number for each target gene comprises the steps of:

a) calculating the difference in quantification cycle (Cq) between the NT and IS for a target gene using the formula$[\text{NT Cq}-\text{IS Cq}]_{Target\ Gene}$;

b) calculating an average difference in Cq between the NT and IS of two concentrations of ESM using the formula $([\text{NT Cq}-\text{IS Cq}]_{ESM\ Concentration\ 1}+[\text{NT Cq}-\text{IS Cq}]_{ESM\ Concentration\ 2})/2=[\text{NT Cq}-\text{IS Cq}]_{ESM}$;

c) calculating a corrected delta Cq using the formula $[\text{NT Cq}-\text{IS Cq}]_{Target\ Gene}-[\text{NT Cq}-\text{IS Cq}]_{ESM}$;

d) obtaining a target gene NT copy number by multiplying $2^{(-corrected\ delta\ Cq)}$ by the known number of input IS copies corresponding to the target gene in the reaction; and e) normalizing the target gene NT copy number to a reference gene loading control gene NT value.

22. The method of claim 17, wherein the samples comprise material having degraded RNA therein.

23. The method of claim 17, wherein the samples comprise formalin fixed paraffin embedded (FFPE) samples.

24. The method of claim 17, wherein the samples comprise fresh-frozen samples.

25. A method to control for inter-experimental variation occurring during two-color RT-qPCR amplification comprising:

i) providing one or more synthetic competitive internal standards (IS), wherein each IS is synthesized to correspond with a unique target gene or reference gene, and wherein known quantities of the one or more IS are formulated into an internal standards mixture (ISM);

j) providing an external standards mixture (ESM) comprising:

(1) one or more purified synthetic native template (NT), wherein each NT is synthesized to correspond with a unique target gene or reference gene; and (2) one or more synthetic competitive internal standards (IS), wherein each IS is synthesized to correspond with a unique target gene or reference gene, wherein known quantities of each purified synthetic NT and IS are formulated into the ESM at a ratio in the range of 10:1 to 1:10;

k) simultaneously performing PCR amplification of each individual gene in reaction mixtures containing two distinct concentrations of the ESM, and primers and fluorometric probes for each individual gene NT and IS, wherein each distinct PCR reaction concentration of ESM further comprises the same fluorometric hydrolysis probes specific for the single gene NT and corresponding IS;

l) while running a two-color RT-qPCR amplification to quantify a target gene using the ISM, simultaneously amplifying two distinct concentrations of ESM, wherein the ESM comprises fluorometric hydrolysis probes for the NT and IS being quantified;

m) correcting a measured copy number for one or more target genes by:

(1) calculating the difference in quantification cycle (Cq) between NT and IS for a target gene ($[\text{NT Cq}-\text{IS Cq}]_{Target\ Gene}$);

(2) calculating an average difference in Cq between NT and IS of two concentrations of ESM (($[\text{NT Cq}-\text{IS Cq}]_{ESM\ Concentration\ 1}+[\text{NT Cq}-\text{IS Cq}]_{ESM\ Concentration\ 2})/2=[\text{NT Cq}-\text{IS Cq}]_{ESM}$);

(3) calculating the corrected delta Cq using the formula $[\text{NT Cq}-\text{IS Cq}]_{Target\ Gene}-[\text{NT Cq}-\text{IS Cq}]_{ESM}$;

(4) obtaining a target gene NT copy number by multiplying $2^{(-corrected\ delta\ Cq)}$ by the known number of input IS copies corresponding to the target gene in the reaction; and (5) normalizing the target gene NT copy number to a reference gene loading control gene NT value, wherein normalizing the target gene NT copy number to a reference gene loading control gene NT value controls for inter-experimental variation occurring during two-color RT-qPCR, as any variation in the observed $[\text{NT Cq}-\text{IS Cq}]_{ESM}$ relative to the expected value of 0 is attributable to the inter-experimental variation.

26. The method according to claim 25, wherein the two-color RT-qPCR amplification is being done on cDNA originated from a sample having degraded RNA therein.

27. The method of claim 26, wherein the sample comprises a formalin fixed paraffin embedded (FFPE) sample.

28. The method of claim 26, wherein the sample comprises a fresh-frozen sample.

29. The method according to claim 25, wherein the inter-experimental variation arises from variation in fluorescence specific activity.

30. The method according to claim 25, wherein the inter-experimental variation arises from the RT-qPCR reaction being conducted on a different machine.

31. The method according to claim 25, wherein the inter-experimental variation arises from variation in equipment and procedures between different laboratories.

* * * * *

```
                          SEQUENCE LISTING


<160> NUMBER OF SEQ ID NOS: 28

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1

gccctgaggc actcttccag                                                20


<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2

tttcgtggat gccacaggac                                                20


<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
```

```
cctggagact ctcagggtcg                                              20


<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4

gcgtttggag tggtagaaat                                              20


<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5

agctgcttag acgctggatt                                              20


<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6

ctaacgttga ggggcatcgt                                              20


<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7

ctcctcaggg cacaggaa                                                18


<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8

cgtggactct tcggagaact ttc                                          23


<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 9

ccttccttcc tgggcatg                                                18
```

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: Synthetic probe

<400> SEQUENCE: 10
ccaaccttcc agggcatc 18

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: Synthetic probe

<400> SEQUENCE: 11
aaacggcggc agaccagc 18

<210> SEQ ID NO 12
<211> LENGTH: 17
<212> TYPE: DNA
<213> ORGANISM: Artificial Sequence
<220> FEATURE:
<223> OTHER INFORMATION: Description of Artificial Sequence: Synthetic probe

<400> SEQUENCE: 12
ttacggcggg tgaccac 17

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic probe

<400> SEQUENCE: 13
tagtggaaaa ccagcagcct 20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic probe

<400> SEQUENCE: 14
atgtggaaat cctgcagcga 20

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: Synthetic probe

<400> SEQUENCE: 15
catcgatcgg gccttgtt 18

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: Synthetic probe

<400> SEQUENCE: 16
ttccgatcgt gccttcta 18

<210> SEQ ID NO 17
<211> LENGTH: 60
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 17
gccctgaggc actcttccag ccttccttcc tgggcatgga gtcctgtggc atccacgaaa 60

<210> SEQ ID NO 18
<211> LENGTH: 60
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 18
gccctgaggc actcttccag ccaaccttcc agggcatcga gtcctgtggc atccacgaaa 60

<210> SEQ ID NO 19
<211> LENGTH: 66
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 19
cctggagact ctcagggtcg aaaacggcgg cagaccagca tgacagattt ctaccactcc 60
aaacgc 66

<210> SEQ ID NO 20
<211> LENGTH: 66
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 20
cctggagact ctcagggtcg attacggcgg gtgaccacca tgacagattt ctaccactcc 60
aaacgc 66

<210> SEQ ID NO 21
<211> LENGTH: 75
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 21
agctgcttag acgctggatt tttttcgggt agtggaaaac cagcagcctc ccgcgacgat 60
gcccctcaac gttag 75

<210> SEQ ID NO 22
<211> LENGTH: 75
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 22
agctgcttag acgctggatt tttttcggga tgtggaaatc ctgcagcgac ccgcgacgat 60
gcccctcaac gttag 75

<210> SEQ ID NO 23
<211> LENGTH: 79
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 23
ctcctcaggg cacaggaaaa catcgatcgg gccttgtttg ctcttaaggg agatctgaaa 60
gttctccgaa gagtccacg 79

<210> SEQ ID NO 24
<211> LENGTH: 79
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 24
ctcctcaggg cacaggaaaa ttccgatcgt gccttctatg ctcttaaggg agatctgaaa 60
gttctccgaa gagtccacg 79

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence: Synthetic probe
<220> FEATURE:
<221> NAME/KEY: modified_base
<222> LOCATION: (1)..(2)
<223> OTHER INFORMATION: a, c, t, g, unknown or other
<220> FEATURE:
<221> NAME/KEY: modified_base
<222> LOCATION: (5)..(10)
<223> OTHER INFORMATION: a, c, t, g, unknown or other
<220> FEATURE:
<221> NAME/KEY: modified_base
<222> LOCATION: (12)..(17)
<223> OTHER INFORMATION: a, c, t, g, unknown or other

<400> SEQUENCE: 25
nnttnnnnnn tnnnnnng 18

<210> SEQ ID NO 26
<211> LENGTH: 58
<212> TYPE: DNA

<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, t, g, unknown or other
<220> FEATURE:
<221> NAME/KEY: modified_base
<222> LOCATION: (22)..(27)
<223> OTHER INFORMATION: a, c, t, g, unknown or other
<220> FEATURE:
<221> NAME/KEY: modified_base
<222> LOCATION: (29)..(34)
<223> OTHER INFORMATION: a, c, t, g, unknown or other
<220> FEATURE:
<221> NAME/KEY: modified_base
<222> LOCATION: (37)..(58)
<223> OTHER INFORMATION: a, c, t, g, unknown or other

<400> SEQUENCE: 26
nnnnnnnnnn nnnnnnnnnn cnnnnnnann nnnnaannnn nnnnnnnnnn nnnnnnnn 58

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (1)..(2)
<223> OTHER INFORMATION: a, c, t, g, unknown or other
<220> FEATURE:
<221> NAME/KEY: modified_base
<222> LOCATION: (5)..(10)
<223> OTHER INFORMATION: a, c, t, g, unknown or other
<220> FEATURE:
<221> NAME/KEY: modified_base
<222> LOCATION: (12)..(17)
<223> OTHER INFORMATION: a, c, t, g, unknown or other

<400> SEQUENCE: 27
nnaannnnnn annnnnnc 18

<210> SEQ ID NO 28
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, t, g, unknown or other
<220> FEATURE:
<221> NAME/KEY: modified_base
<222> LOCATION: (22)..(27)
<223> OTHER INFORMATION: a, c, t, g, unknown or other
<220> FEATURE:
<221> NAME/KEY: modified_base
<222> LOCATION: (29)..(34)
<223> OTHER INFORMATION: a, c, t, g, unknown or other
<220> FEATURE:
<221> NAME/KEY: modified_base
<222> LOCATION: (37)..(58)
<223> OTHER INFORMATION: a, c, t, g, unknown or other

<400> SEQUENCE: 28
nnnnnnnnnn nnnnnnnnnn gnnnnnntnn nnnnttnnnn nnnnnnnnnn nnnnnnnn 58